(12) United States Patent
Henry et al.

(10) Patent No.: US 10,768,080 B2
(45) Date of Patent: Sep. 8, 2020

(54) METHOD OF PURIFYING TUMOR CELLS USING SHEAR STRESS

(71) Applicant: UNIVERSITY OF IOWA RESEARCH FOUNDATION, Iowa City, IA (US)

(72) Inventors: Michael D. Henry, Iowa City, IA (US); J. Matthew Barnes, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 78 days.

(21) Appl. No.: 15/943,187

(22) Filed: Apr. 2, 2018

(65) Prior Publication Data

US 2018/0224359 A1    Aug. 9, 2018

Related U.S. Application Data

(63) Continuation of application No. 14/713,270, filed on May 15, 2015, now abandoned, which is a continuation of application No. 14/006,761, filed as application No. PCT/US2012/030034 on Mar. 22, 2012, now Pat. No. 9,063,118.

(60) Provisional application No. 61/466,983, filed on Mar. 24, 2011.

(51) Int. Cl.
    *G01N 1/40*     (2006.01)
    *B01L 3/00*     (2006.01)
    *G01N 33/50*    (2006.01)
    *G01N 33/574*   (2006.01)
    *C12N 5/09*     (2010.01)
    *G01N 33/487*   (2006.01)
    *G01N 33/48*    (2006.01)

(52) U.S. Cl.
    CPC .......... *G01N 1/40* (2013.01); *B01L 3/50273* (2013.01); *B01L 3/502715* (2013.01); *C12N 5/0693* (2013.01); *G01N 33/487* (2013.01); *G01N 33/5026* (2013.01); *G01N 33/5044* (2013.01); *G01N 33/5091* (2013.01); *G01N 33/574* (2013.01); *B01L 2200/027* (2013.01); *B01L 2200/0647* (2013.01); *B01L 2400/0475* (2013.01); *C12N 2521/00* (2013.01)

(58) Field of Classification Search
    CPC .. G01N 1/40; G01N 1/28; G01N 1/00; G01N 33/487; G01N 33/483; G01N 33/48; G01N 33/00; G01N 33/5026; G01N 33/502; G01N 33/5008; G01N 3/5005; G01N 3/50

USPC ............................................. 435/39, 34, 29
See application file for complete search history.

(56) References Cited

U.S. PATENT DOCUMENTS

| | | | |
|---|---|---|---|
| 9,063,118 B2 | 6/2015 | Henry et al. | |
| 2003/0219713 A1* | 11/2003 | Valencia | G01N 15/1475 435/4 |
| 2003/0221996 A1 | 12/2003 | Svoronos et al. | |
| 2006/0223195 A1* | 10/2006 | Meyer | G01N 33/54393 436/518 |
| 2009/0298067 A1 | 12/2009 | Irimia et al. | |
| 2010/0167384 A1 | 7/2010 | Clemmens et al. | |
| 2014/0274739 A1 | 9/2014 | Rinker et al. | |
| 2015/0307848 A1 | 10/2015 | Henry et al. | |
| 2015/0316456 A1 | 11/2015 | Henry et al. | |

FOREIGN PATENT DOCUMENTS

| | | |
|---|---|---|
| WO | 2013086509 A1 | 6/2013 |
| WO | 2014070776 A1 | 5/2014 |

OTHER PUBLICATIONS

Barnes, James Matthew. "Influence of matrix and fluid microenvironments on cancer cell migration, survival, and metastasis." PhD (Doctor of Philosophy) thesis, University of Iowa, 2011. (Year: 2011).*

Couzon, et al., "Critical stresses for cancer cell detachment in microchannels", European Biophysics Journal 38(8), 1035-1047 (2009).

Hallow, et al., "Shear-induced intracellular loading of cells with molecules by controlled microfluidics", Biotechnol Bioeng 99(4), 846-854 (2008).

Patent Cooperation Treaty, International Search Report and Written Opinion for PCT/US2015/05825, 11 pages, dated Feb. 15, 2016.

Phillips, et al., "Enrichment of Cancer Cells Using Aptamers Immobilized on a Microfluidic Channel", Anal. Chem.81(3), 1033-1039 (2009).

* cited by examiner

*Primary Examiner* — Christine T Mui
(74) *Attorney, Agent, or Firm* — Viksnins Harris Padys Malen LLP

(57) ABSTRACT

Methods for isolating viable cancer cells from a sample that comprises a mixture of cancerous cells and normal (non-cancerous) cells are provided. In the methods, a fluid preparation comprising a mixture of cancerous and normal cells is repeatedly exposed to fluid shear stresses, whereby the repeated exposure to the fluid shear stresses preferentially imparts fluid shear stress-resistance to the cancerous cells.

9 Claims, 24 Drawing Sheets

METHOD OF PURIFYING TUMOR CELLS USING SHEAR STRESS

CROSS REFERENCE TO RELATED APPLICATIONS

This application is a continuation of U.S. patent application Ser. No. 14/713,270, filed May 15, 2015, which is a continuation of U.S. patent application Ser. No. 14/006,761, filed Oct. 15, 2013, which issued as U.S. Pat. No. 9,063,118, which is a National Stage Entry under 35 U.S.C. § 371 of International patent application number PCT/US2012/030034, filed Mar. 22, 2012, which claims the benefit of U.S. provisional patent application No. 61/466,983, filed on Mar. 24, 2011, the entire contents of which are all incorporated herein by reference.

REFERENCE TO GOVERNMENT RIGHTS

This invention was made with government support under CA130916 awarded by the National Institutes of Health and under W81XWH-10-1-0313 awarded by the U.S. Army Medical Research and Material Command. The government has certain rights in this invention.

BACKGROUND

Metastasis is the leading cause of mortality in patients with epithelial cancers. This complex process involves the detachment of cells from the primary tumor, invasion into surrounding tissue, entrance to and survival within the bloodstream, extravasation, and, finally, survival and proliferation at the secondary site. It is believed that metastasis is an inefficient process. Clinically, metastatic inefficiency can be appreciated by considering that many tumors continuously shed cancer cells into the bloodstream on a daily basis, giving rise to a population of circulating tumor cells (CTCs), yet only a small number of these go on to colonize distant sites in a process which may take decades.

Some groups have reported that survival within the bloodstream and subsequent extravasation are completed efficiently by most tumor cells and that the ability to survive and grow at secondary sites is what determines the aggressiveness of a cell type [Luzzi, K. J., et al., *Multistep nature of metastatic inefficiency: dormancy of solitary cells after successful extravasation and limited survival of early micrometastases*. Am J Pathol, 1998. 153(3): p. 865-73., Koop, S., et al., *Fate of melanoma cells entering the microcirculation: over 80% survive and extravasate*. Cancer Res, 1995. 55(12): p. 2520-3., Podsypanina, K., et al., *Seeding and propagation of untransformed mouse mammary cells in the lung*. Science, 2008. 321(5897): p. 1841-4., Tsuji, T., et al., *Epithelial-mesenchymal transition induced by growth suppressor p12CDK2-AP1 promotes tumor cell local invasion but suppresses distant colony growth*. Cancer Res, 2008. 68(24): p. 10377-86.]. In an effort to study the fate of CTCs, other groups have conducted studies to monitor the destination and viability of tumor cells injected systemically into mice. These authors concluded that the majority of circulating tumor cells are rapidly destroyed in the bloodstream by shear force [Fidler, I. J., *Metastasis: quantitative analysis of distribution and fate of tumor emboli labeled with 125 I-5-iodo-2'-deoxyuridine*. J Natl Cancer Inst, 1970. 45(4): p. 773-82., Fidler, I. J., *Biological behavior of malignant melanoma cells correlated to their survival in vivo*. Cancer Res, 1975. 35(1): p. 218-24.] and/or by deformation following size restriction in the microvasculature [Weiss, L., *Deformation-driven, lethal damage to cancer cells. Its contribution to metastatic inefficiency*. Cell Biophys, 1991. 18(2): p. 73-9., Weiss, L., et al., *Lethal deformation of cancer cells in the microcirculation: a potential rate regulator of hematogenous metastasis*. Int J Cancer, 1992. 50(1): p. 103-7.]. This led to the longstanding assumption that cell death within the circulation is a major contributor to metastatic inefficiency. Observations of significant cell loss following injection into mice have been reported by others as well [Kienast, Y., et al., *Real-time imaging reveals the single steps of brain metastasis formation*. Nat Med, 2010. 16(1): p. 116-22., Al-Mehdi, A. B., et al., *Intravascular origin of metastasis from the proliferation of endothelium-attached tumor cells: a new model for metastasis*. Nat Med, 2000. 6(1): p. 100-2.].

During hematogenous dissemination, CTCs encounter a wide range of shear stresses (1-$10^5$ dyn/s) [Schneider, S. W., et al., *Shear-induced unfolding triggers adhesion of von Willebrand factor fibers*. Proc Natl Acad Sci USA, 2007. 104(19): p. 7899-903., Reneman, R. S., T. Arts, and A. P. Hoeks, *Wall shear stress—an important determinant of endothelial cell function and structure—in the arterial system in vivo. Discrepancies with theory*. J Vasc Res, 2006. 43(3): p. 251-69.]. Shear stress is a major component of the vascular microenvironment and has important biological implications; for example, endothelial cells are fine-tuned to shear stress and variations in the magnitude or frequency of shear forces have effects on the signaling, gene expression, and survival of these cells [Malek, A. M., S. L. Alper, and S. Izumo, *Hemodynamic shear stress and its role in atherosclerosis*. JAMA, 1999. 282(21): p. 2035-42., Malek, A. and S. Izumo, *Physiological fluid shear stress causes downregulation of endothelin-1 mRNA in bovine aortic endothelium*. Am J Physiol, 1992. 263(2 Pt 1): p. C389-96.]. Shear stress has also been shown to induce changes in the gene expression and adhesive properties of both leukocytes and cancer cells [Okuyama, M., et al., *Fluid shear stress induces actin polymerization in human neutrophils*. J Cell Biochem, 1996. 63(4): p. 432-41., Avvisato, C. L., et al., *Mechanical force modulates global gene expression and beta-catenin signaling in colon cancer cells*. J Cell Sci, 2007. 120(Pt 15): p. 2672-82., Stroka, K. M. and H. Aranda-Espinoza, *A biophysical view of the interplay between mechanical forces and signaling pathways during transendothelial cell migration*. FEBS J, 2010. 277(5): p. 1145-58.]. Epithelial cells, from which carcinomas are derived, reside in environments with much lower shear stress than found in the bloodstream [Althaus, M., et al., *Mechano-sensitivity of epithelial sodium channels (ENaCs): laminar shear stress increases ion channel open probability*. The FASEB journal: official publication of the Federation of American Societies for Experimental Biology, 2007. 21(10): p. 2389-99.]. It is thus reasonable to believe such cells would be particularly susceptible to destruction by hemodynamic shear forces, as compared to naturally circulating cells (i.e. red blood cells and leukocytes). One early study examined death of B16 melanoma cells subjected to shear stress using a viscometer [Brooks, D. E., *The biorheology of tumor cells*. Biorheology, 1984. 21(1-2): p. 85-91.]. This report showed dose-dependent killing of cells, however, the earliest viability time points analyzed were after one hour of shear stress exposure.

SUMMARY

Methods for purifying viable cancerous epithelial cells in an in vitro fluid preparation comprising viable cancerous epithelial cells, viable normal epithelial cells, and extracellular calcium are provided. In some embodiments, the methods comprise: applying an initial pulse of fluid shear stress to the preparation, wherein the initial pulse of fluid shear stress induces a fluid shear stress resistance in the viable cancerous epithelial cells; and subsequently applying one or more additional pulses of fluid shear stress to the preparation comprising the fluid shear stress-resistant viable cancerous epithelial cells, whereby the ratio of viable cancerous epithelial cells to viable normal epithelial cells in the preparation is increased.

Also provided are methods for detecting cancerous epithelial cells in a mammalian subject. In some embodiments, the methods comprise: obtaining a cell sample from the subject, the cell sample comprising cancerous epithelial cells and normal epithelial cells; forming a fluid preparation comprising the cancerous epithelial cells, the normal epithelial cells and extracellular calcium; applying an initial pulse of fluid shear stress to the preparation, wherein the initial pulse of fluid shear stress induces a fluid shear stress resistance in the cancerous epithelial cells; subsequently applying one or more additional pulses of fluid shear stress to the preparation comprising the fluid shear stress-resistant viable cancerous epithelial cells, whereby the ratio of viable cancerous epithelial cells to viable normal epithelial cells in the preparation is increased; and subsequently measuring the amount of viable cancerous epithelial cells in the preparation.

Still further provided are methods for preparing a fluid preparation comprising circulating tumor cells for a prognostic assay. In some embodiments, the methods comprise: obtaining a blood sample from the subject, the blood sample comprising circulating tumor cells and normal epithelial cells; forming a fluid preparation comprising the circulating tumor cells, the normal epithelial cells and extracellular calcium; applying an initial pulse of fluid shear stress to the fluid preparation, wherein the initial pulse of fluid shear stress induces a fluid shear stress resistance in the circulating tumor cells; subsequently applying one or more additional pulses of fluid shear stress to the fluid preparation, whereby the ratio of circulating tumor cells to viable normal epithelial cells in the preparation is increased; and subsequently conducting an assay on the preparation, the assay providing a cancer prognosis for the subject based on the viable cancerous epithelial cells.

BRIEF DESCRIPTION OF THE DRAWINGS

Illustrative embodiments of the invention will hereafter be described with reference to the accompanying drawings.

FIG. 1A: Endpoint viability after 10 passages at indicated flow rate. (*, $p<0.001$ vs. 0 control. One way ANOVA, Bonferroni's post-test; for each flow rate, n=5 using syringe pump) FIG. 1B: Survival over repeated passages at 20 and 250 µL/sec. ($p<0.01$, *** $p<0.001$ vs. 20 µL/sec. Repeated measures ANOVA, Bonferroni's post-test; for each flow rate n=5 using syringe pump). FIG. 1C: After 10 passages at 250 µL/sec, cell viability quantified via BLI was compared using WST-1 assay and clonogenic plating (Using one-way ANOVA, there are not significant differences between the results obtained from these three methods; for each assay n=4 using manual method). FIG. 1D: To test the effects of culture conditions on shear stress survival, PC-3 cells were prepared under the following conditions: "$5×10^4$ vs. $5×10^5$ cells/mL", from cells grown to 70% confluence; "low vs. medium vs. high confluence", from cells grown to 20-30%, 50-60%, or 100% confluence, respectively, prior to suspension at $5×10^5$ cells/mL; "fresh vs. sheared", trypsinized cells, grown to ~70% confluence, were suspended in "fresh" media or were suspended in "sheared" media (cell-free media collected from cells sheared ten times at 250 µL/sec); "versene", cells were suspended non-enzymatically to $5×10^4$ cells/mL and compared to cells prepared similarly using trypsin. (No statistically significant differences using one-way ANOVA, All experiments n=4 using manual method).

FIG. 2A: A panel of transformed and normal epithelial and blood cells was compared for survival after 10 passages of fluid shear stress at 250 µL/sec. Cancer cell lines exhibited robust resistance over other epithelial cell types. *, $p<0.001$ vs. all cancer cell lines; #, $p<0.001$ vs. RWPE-1; ††, $p<0.001$ vs. all non-blood cells (one way ANOVA, Bonferroni post tests n=3 for blood cells by syringe pump method, n=6 for all other lines using manual method). FIG. 2B: The viability of all cells in A at every other passage. FIG. 2C: The rate of cell death per passage of all epithelial cell types represented in A. Note the rate of cancer cell death significantly reduces and stabilizes after the second passage, whereas non-transformed cells remain constant. While primary cells appear biphasic, they lose nearly all viability over the first two passages. *, $p<0.001$ vs. passages 1 to 2 of cancer cells; # $p<0.05$ vs. passages 1 to 2 of primary cells (one way ANOVA, Bonferroni post tests). FIG. 2D: To control for detachment-induced cell death, PC-3 and primary cells were held in suspension at room temperature without shear stress treatment for up to one hour. Loss of viability due to detachment over the first 30 minutes is insignificant by one-way ANOVA, n=5 for each cell line).

FIG. 4B: Histogram plats of PI uptake of the data shown in FIG. 4A. FIG. 4C: To confirm that the P1+P2 gate represented only viable cells, and to eliminate the possibility that Pt-dead cells were contributing to our Pt gate, the vital stain Calcein AM was used and confirmed that the P1+P2 gate was predominantly constituted by viable cells (p1 99.8%, p10 99.2%). FIG. 4C When PI was added prior to passage 6 (pre-6), 8 (pre-8), or 10 (pre-10), less of the viable population of cells accumulated the dye with the first passage with PI. With subsequent passages displayed a plateau of accumulation, much as see in the late passages in constant presence of PI. This reflects a shear force-resistant phenotype that exists after 1-2 shear passages in a subset of remaining viable cells, and explains the biphasic change in cell viability observed over 10 passages (FIG. 2B). (*p<0.05 vs. 1 constant; for each condition, n=8 using syringe pump).

FIG. 5A: PC-3 cells suspended in complete medium, calcium-free PBS, or PBS plus calcium (129.4 µg/mL final concentration) were subjected to shear stress at 250 µL/sec. The absence of calcium leads to significantly increased cell death whereas cells suspended in calcium-supplemented PBS exhibit cell survival similar to that of cells in media. FIG. 5B: The same experiment as described in FIG. 5A was performed at 20 µL/sec. In complete medium, this flow rate induces little loss of viability in PC-3 cells; however in calcium-free PBS, cell death is rapid and linear. *p<0.05, p<0.01, * p<0.001 vs. complete media, Repeated measures ANOVA, Bonferroni's post-test; for each condition, n=6 using syringe pump).

FIG. 6A: PC-3 cells were treated with 20 nM cytochalasin-D for one hour before exposure to the shear stress protocol. FIG. 6B: MDA.MB.231 cells were treated with 20 nM cytochalasin-D for one hour before exposure to the shear stress protocol. Cytochalasin-D treated cells are much more susceptible to shear stress than DMSO control cell suspensions. p<0.01, * p<0.001 vs. DMSO control (one way ANOVA, Bonferroni post test; for each condition, n=4 using manual method).

FIG. 10A displays the endpoint viability and FIG. 10B displays the viability over repeated passages. For each cell line, survival is represented as percent viability of non-shear treated cells which are held in suspension for the duration of the assay. Cell lines obtained from experimental metastases in mice were included for PC-3 (AD, adrenal gland; LD, liver), MDA.MB.231 (LuD, lung), B16f0 (B16f10, 10-times serially passaged intravenously to lung), and 22Rv1 (BD, long bone). These in vivo derivatives do not exhibit increased shear stress resistance. For each cell line experiments were done at least three times using the pump method.

FIG. 13A: Viability at every other passage. FIG. 13B: Comparison of PrEC, HMEC, and PC-3 survival after ten passages at 20 µL/sec.

FIG. 14A: Suspensions of PC-3 and PrEC were labeled with calcein AM (CAM) and cytotracker orange, respectively, and mixed ~1:1. Before (P.0) and after ten passages (P.10) of FSS, 10,000 fluorescent events were counted using flow cytometry. FIG. 14B: 25 µL of mixed (PC-3:PrEC) cell suspension was plated into collagen 1-coated 8-well chamber slides before (P.0) and after ten passages (P.10) of FSS. These cells were allowed to adhere overnight and were then fixed in 4% paraformaldehyde for 10 minutes. The ratio of calcein AM positive to negative cells is shown.

DETAILED DESCRIPTION

Figure 1A:
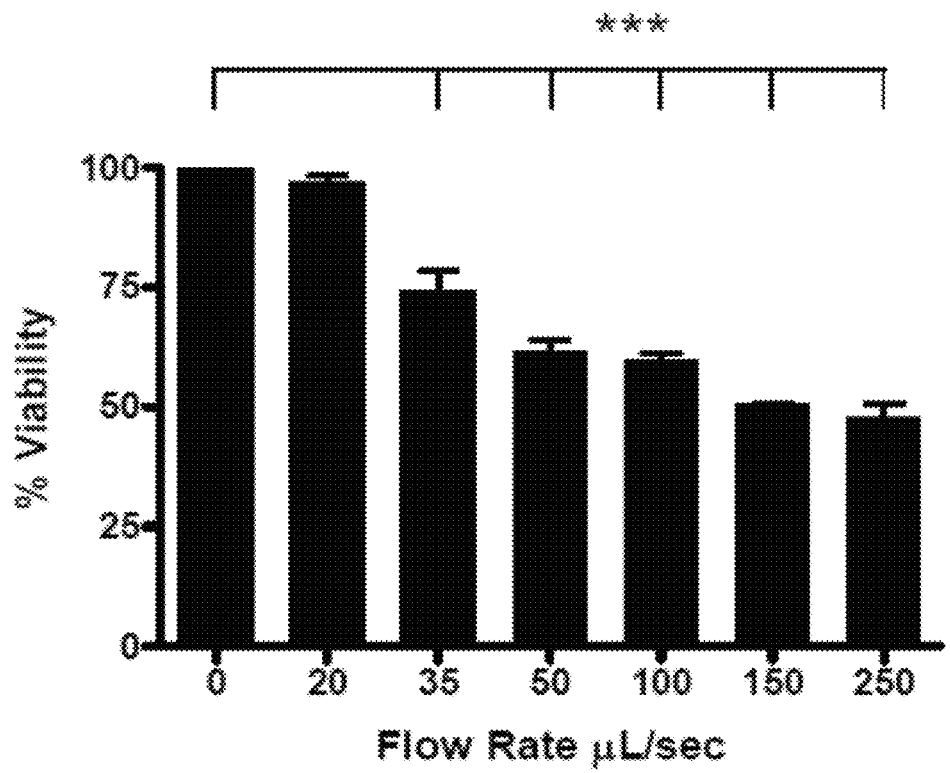
FIGS. 1A-1D show that an in vitro model of fluid shear stress induces cell death in a dose-dependent fashion. Suspensions of PC-3 cells were subjected to repeated shear stress at increasing flow rates, corresponding to a range in shear forces from 509-6.36×10³ dyn/cm² (see Table 1), and monitored for changes in viability. Survival is represented as percent viability of non-shear treated cells which are held in suspension for the duration of the assay.
Figure 1B:
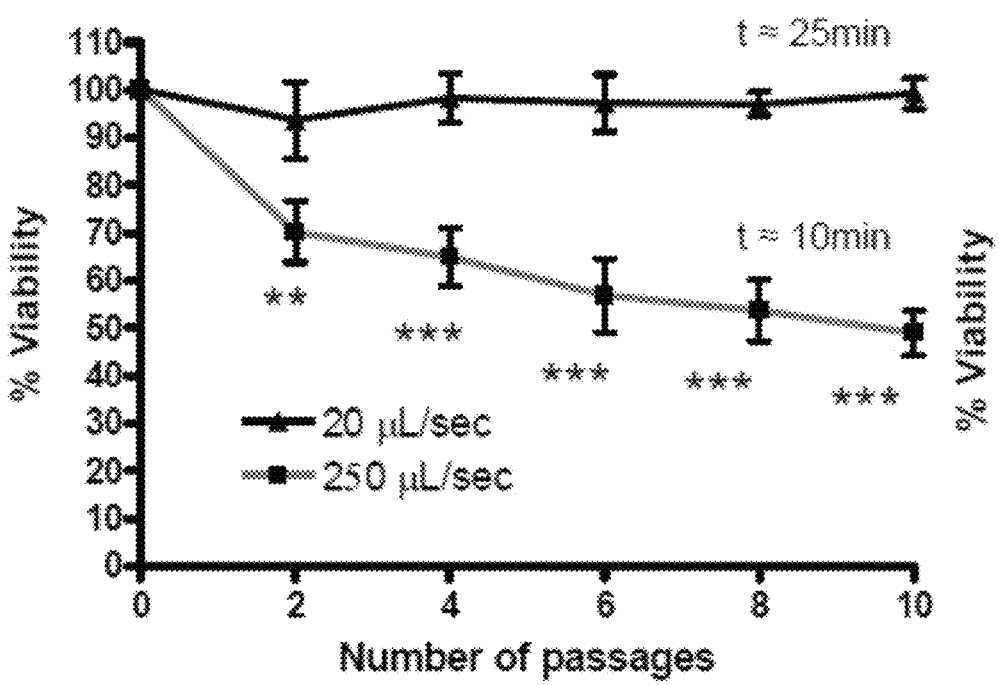

Methods for isolating viable cancer cells from a sample that comprises a mixture of cancerous cells and normal (non-cancerous) cells are provided. Also provided are methods for detecting cancerous cells in a subject and methods for preparing patient samples, such as blood samples, for prognostic or diagnostic assays predictions based on the detection and/or concentration of cancerous cells in the sample. A motivation behind the methods may be attributed, at least in part, to the discovery that fluid shear stress can be used to selectively kill normal cells in a preparation that includes both normal and cancerous cells. Moreover, in addition to the ability to selectively kill normal cells relative to cancerous cells, the present methods may provide the ability to selectively kill cancerous cells based on their level of metastatic potential. As such, the methods can be used to enrich a preparation with more aggressive and, thus, more prognostically valuable cancer cells.

In the methods, a liquid preparation comprising a suspension of cancer cells is repeatedly exposed to fluid shear stresses. For example, the preparation can be passed through a conduit, desirably at a substantially constant flow rate, multiple times, whereby the repeated exposure to the resulting fluid shear stresses imparts an increased resistance to fluid shear stress to the cancer cells. The normal cells in the preparation do not experience an increase in their resistance to fluid shear stress or experience a lower increase than the cancerous cells and, therefore, are susceptible to magnitudes of shear stress much lower than those required to kill cancer cells. The resistance to shear stress is not believed to be a stable, genetic trait, but rather a transient, adaptive response that is able to develop in the presence of extracellular calcium.

In one embodiment, the methods provide for the purification of viable cancerous cells in a fluid preparation comprising a mixture of viable cancerous cells, viable normal cells, and extracellular calcium. At the outset, the preparation can be characterized by an initial ratio of viable cancerous cells to viable normal cells. In this embodiment, the method comprises the steps of applying an initial pulse of fluid shear stress to the preparation, wherein the initial pulse of fluid shear stress induces a fluid shear stress resistance in the viable cancerous cells. Subsequently one or more additional pulses of fluid shear stress are applied to the preparation, which now comprises the fluid shear stress-resistant viable cancerous cells. As a result of the application of the fluid shear stresses to the preparation, the ratio of viable cancerous cells to viable normal cells in the preparation is increased and the preparation is thereby purified. Optionally, the purified preparation can further processed by separating the viable cells from the non-viable cells and/or by separating the cancerous cells from the normal cells.

As a result of the present methods, the cancerous cells in a preparation may be observed to exhibit a biphasic viability behavior, wherein after the initial resistance-inducing pulse, the observed loss in cell viability is significantly reduced for subsequent pulses.

The present methods can further provide for the detection and quantification of cancerous cells in a subject, such as a human patient, with cancer. In one embodiment of such a method, a cell sample comprising cancerous cells and normal cells is obtained from the subject and a fluid preparation comprising the cancerous and normal cells in the presence of extracellular calcium is prepared. Here again, the method comprises the steps of applying an initial pulse of fluid shear stress to the preparation, wherein the initial pulse of fluid shear stress induces a fluid shear stress resistance in the viable cancerous cells. Subsequently one or more additional pulses of fluid shear stress are applied to the preparation, which now comprises the fluid shear stress-resistant viable cancerous cells. As a result of the application of the fluid shear stresses to the preparation, the ratio of viable cancerous cells to viable normal cells in the preparation is increased and the preparation is thereby purified. The amount (e.g., concentration) of viable cancerous cells in the purified preparation is then measured.

The results of the measurement can be used, for example, in diagnostic or prognostic assays to assess the likely health outcome for the subject from whom the cell sample was taken. Thus, the present methods provide a relatively simple, relatively low-cost method for providing preparations that are enriched in viable cancerous cells relative to normal (non-cancerous cells) and, as such, are well-suited for use in clinical assays. For example, the results of measurements taken on purified preparations can be correlated to the likelihood of relapse or metastasis in a patient.

By way of illustration, the present methods can be used to purify a preparation comprising a blood sample comprising CTCs for a patient with breast cancer prior to surgery and correlating higher numbers of circulating viable cancer cells with an increased likelihood of breast cancer relapse. Similarly, the present methods can be used to purify a preparation comprising CTCs from a patient with non-small cell lung carcinoma after said patient has had surgery for removal of the carcinoma and correlating higher numbers of circulating viable cancer cells with an increased likelihood of cancer relapse.

The types cancerous and normal epithelial cells that can be subjected to the present methods cover a broad range of mammalian (e.g., human) cells. The preparations comprising the cells can comprise, for example, blood samples, or extracts from blood samples, containing CTCs. Alternatively, the preparation comprising the cells can be prepared from tissue samples. For example, the preparations can comprise suspensions of tumor cells obtained from the biopsy of a solid tumor.

The methods are general and may be conducted on a preparation to isolate cancer cells of any type. Examples of the types of cells that may be present in the preparations include normal and cancerous prostate cells, breast cells, pancreatic cells, colon cells, ovarian cells, plasma cells, lung cells, adrenal cells, liver cells, lymphocyte cells and combinations thereof.

The preparations comprising the cancerous and normal cells can be subjected to pulses of fluid shear stress by passing them through a conduit in, for example, a microfluidic device. Examples of suitable conduits can include, for example, a capillary tube or a needle. The preparations are desirably passed through the conduit at a constant or substantially constant rate. This can be accomplished, for example, using a mechanical pump or by hand—as in the case of a syringe.

As discussed above, an initial pulse of fluid shear stress is applied to the preparation in order to induce an increased resistance to fluid shear stress-induced cell death to the cancerous cells that survive the initial pulse or pulses. By way of clarification, the term 'initial pulse' is not intended to imply that only a single 'initial pulse' can be applied. Instead the term 'initial pulse' refers to a pulse that is used to provide a cell that has been subjected to that pulse with an increased resistance to subsequently applied fluid shear stresses. Thus, an initial pulse is a fluid shear stress resistance-inducing pulse. In the present methods more than one 'initial pulse' may be necessary or desirable. Therefore, the phrase "applying an initial shear stress to a preparation" does not preclude the possibility of applying more than one initial shear stress to the preparation. Further, in some embodiments, the initial pulse (or pulses) and the subsequent additional pulses are applied in vitro. However, if the sample from which the preparation is prepared has already been subjected to an stress resistance-inducing pulse in vivo by virtue of its having experienced a shear stress during circulation and the preparation is processed sufficiently rapidly (i.e., rapidly enough that the stress resistance has not subsided), then the initial pulse may actually be an in vivo pulse.

Both the strength (i.e., the level of shear stress) and the duration of the pulse will affect cell viability in the preparation. Therefore, it is advantageous to select a pulse strength and duration that are sufficient to induce an increased fluid shear stress resistance without reducing the concentration of viable cancerous cells in the preparation to a level that is unacceptable for its intended purpose.

For the purposes of this disclosure, fluid shear stress can be measured by the wall shear stress experienced at the wall of a conduit through which a fluid preparation is passed, calculated using Poiseuille's equation, as described in Example 1, below.

The magnitude of the fluid shear stresses to which the preparation is subjected can vary over a wide range, which includes high and/or supra-physiologic levels (i.e., levels of fluid shear stress that are higher than would be experienced in human circulation). By way of illustration, in some embodiments, the magnitude of the initial pulse(s) of fluid shear stress is in the range from about 300 to about 6500 dyn/cm$^2$. This includes embodiments in which the magnitude of the initial pulse(s) of fluid shear stress is in the range from about 500 to about 6500 dyn/cm$^2$ and further includes embodiments in which the magnitude of the initial pulse(s) of fluid shear stress is in the range from about 700 to about 6000 dyn/cm$^2$.

Like the magnitude of the pulses of fluid shear stress, the duration of the pulses of fluid shear stress used in the present methods can vary over a considerable range. In general, the duration should be long enough to impart a fluid shear stress-resistance to the cancerous cells in the preparation without reducing the number of viable cancerous cells in the preparation to an unacceptably-low value. This can be accomplished with very short pulses, which allows the methods to be carried out rapidly. By way of illustration, in some embodiments, the initial pulse(s) of fluid shear stress has a duration of no greater than about 20 msec. This includes embodiments in which the initial pulse(s) of fluid shear stress has a duration of no greater than about 15 msec. For example, in some embodiments, the initial pulse(s) of fluid shear stress has a duration in the range from about 0.5 msec to about 15 msec.

The one or more additional pulses of fluid shear stress applied to the preparation after the one or more resistance-inducing initial pulses can be used to increase the ratio of viable cancerous cells to viable normal cells in the preparation. Because the fluid shear stress resistance imparted by the initial pulses can diminish over time, the additional pulses should be applied prior to the loss of the induced fluid shear stress-resistance. Thus, in some embodiments, at least the first of the one or more additional pulses are applied within no more than one hour after the initial pulse. This includes embodiments in which at least the first of the one or more additional pulses are applied within no more than 15 minutes after the initial pulse and further includes embodiments in which at least the first of the one or more additional pulses are applied within no more than five minutes after the initial pulse. In some embodiments all of the one or more additional pulses are applied within these time windows.

The magnitude and duration of the additional pulses of fluid shear stress can be the same as, similar to, or different from those of the initial pulse of fluid shear stress. Thus, in some embodiments, the additional pulse(s) of fluid shear stress is in the range from about 300 to about 6500 dyn/cm$^2$. This includes embodiments in which the additional pulse(s) of fluid shear stress is in the range from about 500 to about 6500 dyn/cm$^2$ and further includes embodiments in which the additional pulse(s) of fluid shear stress is in the range from about 700 to about 6000 dyn/cm$^2$. In some embodiments, the initial pulse applies a lower level of fluid shear stress that than the additional pulses. For example, the initial pulses may apply a physiologic level of fluid shear stress, while the one or more additional pulses apply a supra-physiologic level of fluid shear stress.

In some embodiments, the additional pulse(s) of fluid shear stress has a duration of no greater than about 20 msec. This includes embodiments in which the additional pulse of fluid shear stress has a duration of no greater than about 15 msec. For example, in some embodiments, the additional pulse(s) of fluid shear stress have a duration in the range from about 0.5 msec to about 15 msec.

The number of additional pulses can be selected to provide a desired ratio or maximized ratio of viable cancerous cells to viable normal cells in the preparation. By way of illustration, in various embodiments, the methods can use ≤100, ≤50, ≤20, ≤10 or ≤5 additional pulses. For example, in some embodiments, 2-50, 2-20 or 2-10 additional pulses are applied.

The magnitude of the initial and additional pulses of fluid shear stress can be selected such that they provide at least a minimum acceptable level of cancerous cell viability after processing and/or such that they provide a desired enhancement in the ratio of cancerous to normal cells in the preparation. For example, lower fluid shear stresses (e.g., ≤1000 dyn/cm$^2$) can be used to retain a higher overall cell viability, whereas higher fluid shear stresses (e.g., ≥400 dyn/cm$^2$) can be used to provide a higher degree of selective killing of normal cells and, therefore, a greater ratio of cancerous to normal cells.

Generally, the duration of the pulses, the magnitude of the pulses and the number of pulses can be tailored to provide a desired ratio of viable cancerous cells to viable normal cells, or to provide at least a minimum cancerous cell viability, as measured substantially immediately after the additional pulse sequence has been carried out. Thus, by way of illustration, these variable can be selected to provide a ratio of viable cancerous cells to normal cells of at least 2:1, at least 3:1 or at least 10:1 and/or to provide a cancerous cell viability of at least 30%, at least 50% or at least 80%.

Once a fluid preparation has been purified using the present methods, the concentration of viable cancerous cells can be measured and, optionally, quantified. Quantification can entail, for example, counting the number of cells using a method such as Fluorescence Activated Cell Sorting (FACS), or measuring the percent cell viability. Various illustrative methods for measuring cell viability are presented in the examples that follow. For the purposes of this disclosure, the percent of cell viability in a cell sample is determined relative to a control sample composed of the same types of cells in the same preparation that has been maintained, unexposed to fluid shear stresses, for the duration of the fluid shear stress-based purification process. If the reduction in cell viability resulting from the purification process is to be quantified, it is desirable to measure the percent viability substantially immediately after the purification process is completed. That is, before natural cell death occurs to a degree significant enough to alter the measurement.

The purification methods have the capability to substantially increase the ratio of viable cancerous cells to viable normal cells in a preparation comprising both. For example, in some embodiments, the ratio of viable cancerous cells to viable normal cells in the purified preparation is at least doubled relative to the ratio prior to purification. This includes embodiments in which the ratio of viable cancerous cells to viable normal cells in the purified preparation is at least tripled relative to the ratio prior to purification and further includes embodiments in which the ratio is increased by at least a factor of five, at least a factor of 8 or at least a factor of 10.

The methods also have the capability of significantly reducing the percent of viable normal cells in a in a preparation without substantially reducing the percent of viable cancerous cells. For example, in some embodiments, the methods provide a purified preparation, wherein the percent viability for the normal cells is no greater than 5% and the percent viability for the cancerous cells is at least 40%. This includes embodiments of the methods that provide a purified preparation, wherein the percent viability for the normal cells is no greater than 10% and the percent viability for the cancerous cells is at least 70%.

The devices that have been described herein for carrying out the methods are also provided. In one embodiment, a device for applying fluid shear stress to a fluid preparation comprises a conduit configured to contain the fluid preparation, a pump configured to pass the fluid preparation through the conduit, and a flow controller configured to control the rate of flow of the fluid preparation through the conduit, wherein the device is configured to apply one or more pulses of fluid shear stress to the fluid preparation via the pump and flow controller, the one or more pulses sufficient to increase the ratio of cancerous cells to normal cells in the fluid preparation. In some embodiments, the device is configured to apply an initial pulse of fluid shear stress sufficient to induce a fluid shear stress resistance in cancerous cells in the fluid preparation and to subsequently apply one or more additional pulses of fluid shear stress to the fluid preparation. In some embodiments, the device is configured to pass the fluid preparation through the conduit at a substantially constant flow rate. Any of the fluid preparations described herein may be used, e.g., a fluid preparation comprising cancerous epithelial cells, normal epithelial cells and extracellular calcium. The device may be configured to apply any number of pulses of fluid shear stress (e.g., initial pulses, additional pulses) having any of the magnitudes, durations and timings described herein. The device may be configured to apply pulses of fluid shear stress sufficient to provide any of the ratios of cancerous cells to normal cells and/or levels of cancerous cell viability and/or levels of normal cell viability described herein.

EXAMPLES

The following examples illustrate the usefulness of the present methods for detecting, quantifying, purifying and/or isolating cancerous epithelial cells from preparations comprising circulating tumor cells and normal cells. The examples present possible theories and hypothesis in support of the present methods. However, the inventors do not intend to be bound to any particular theory of the inventions, and the theories presented here are not intended to restrict the claimed subject matter.

Example 1

This example illustrates the use of the present methods to purify a preparation prepared from a blood sample comprising CTCs.

Materials and Methods

Cell Lines

All cancer cell lines were obtained from the ATCC and were transduced with an integrating retrovirus encoding firefly luciferase under control of the CMV promoter (pGEM, Promega). Cells were grown in the ATCC-recommended media supplemented with 10% fetal bovine serum and 1% non-essential amino acids. For maintenance of the retrovirus-gene expression, all cells containing this construct were maintained in 200 μg/mL Genetecin (Invitrogen). Primary prostatic and mammary epithelial cells were obtained from Clontech and were cultured in their commercial defined media. For all experiments, cells were grown to ~75% confluence and harvested by trypsinization following neutralization and suspension in complete medium.

Human and Mouse Blood

To obtain whole human blood, fresh leuko-reduction cones were collected from the University of Iowa Hospitals and Clinics DeGowan Blood Center. Cones were flushed in direction of filtration with normal saline (0.99% NaCl) to reduce red blood cell (RBC) content. Diluted RBCs were collected and brought to a concentration of $5 \times 10^5$ cells/mL and used in shear stress experiments. To isolate leukocytes, cones were then eluted in the direction opposite of filtration using 50 mL ACK buffer (150 mM $NH_4Cl_4$, 10 mM $KHCl_3$, 0.10 mM ETDA, pH 7.4), which osmotically lyses remaining RBCs. After 15 minutes of incubation at room temperature, cells were centrifuged at 100RCF for 5 minutes, resuspended in 1 mL PBS+xM calcein AM viability dye (Invitrogen), and incubated for an 15 minutes at room temperature. 9 mL of ACK buffer was added to this cell suspension, centrifuged once more as above, and brought to a final concentration of $5 \times 10^5$ cell s/mL in DMEM (Gibco) without supplements.

For whole mouse blood, sub-mandibular bleeds were performed on adult Bl/6 mice. Blood was collected in EDTA-treated tubes (BD biosciences) and diluted using normal saline to a concentration of $5 \times 10^5$ cells/mL prior to shear stress treatment.

Cell Size Analysis

Cells were suspended to a concentration of $5 \times 10^5$ cell/mL and analyzed on a Coulter Counter (Beckman Coulter) at a 1:100 dilution in Isoton II (Beckman Coulter). Size analysis was performed using Z2 Acucomp software (Beckman Coulter). Gates were set to exclude cellular debris and aggregates following the manufacturer's instructions. At least three separate cultures for each cell line were counted and sized in triplicate. Data was plotted using Prism Graph Pad software and cell lines were compared based on mean cell volume. Paired, two-tailed t-tests were used for analysis of statistical significance.

Shear Stress Equations

Figure 12:
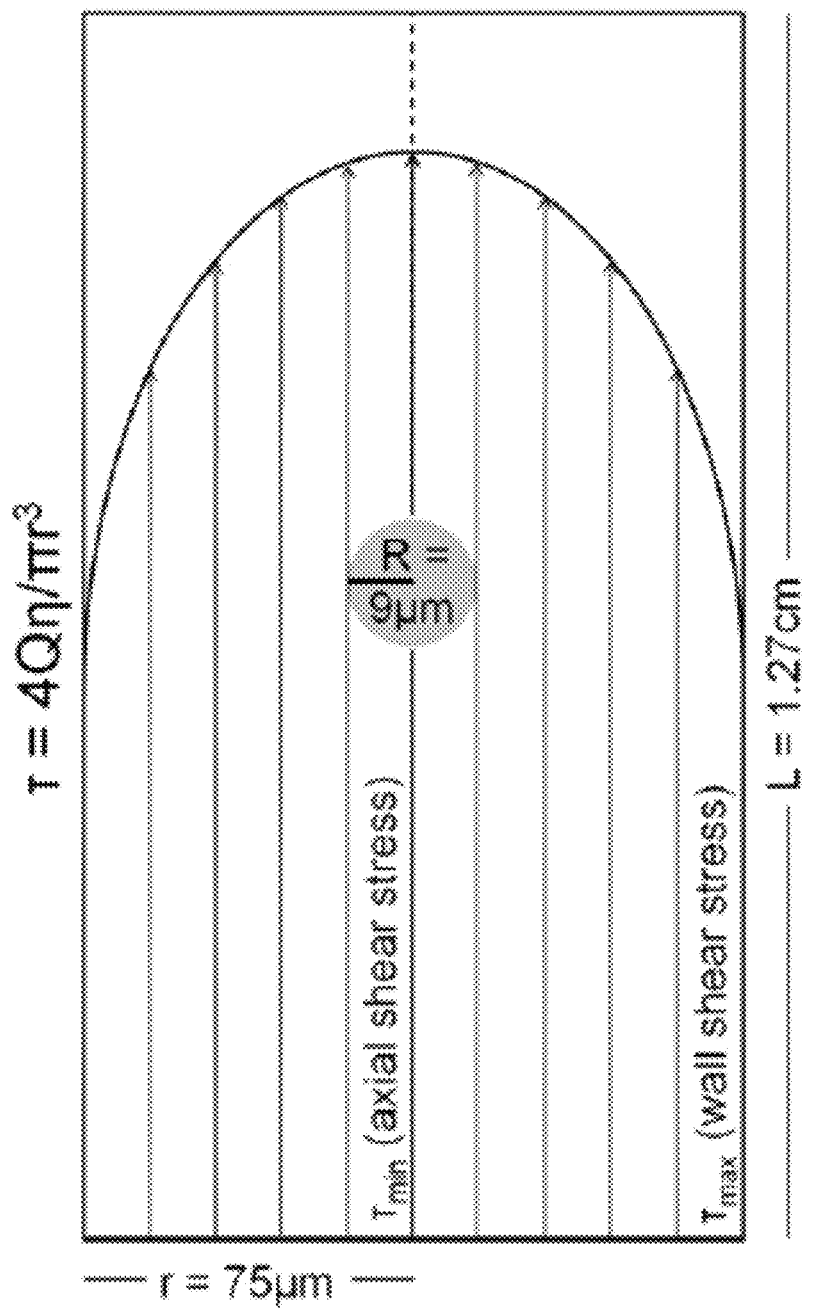
FIG. 12: A schematic scale illustration of a PC-3 cell subjected to FSS in a conduit.

Wall shear stress was calculated using Poiseuille's equation, $\tau = 4 Q\eta/\pi r^3$ [Davies, P. F., Hemodynamic shear stress and the endothelium in cardiovascular pathophysiology. Nat Clin Pract Cardiovasc Med, 2009. 6(1): p. 16-26.], where $\tau$ is shear stress in $dyn/cm^2$; Q is flow rate in $cm^3/s$; $\eta$ is the viscosity of the medium (0.01 dyn/cm/s for culture media);

and r is the radius of the needle (30GA average internal radius=$7.94 \times 10^{-3}$ cm). FIG. 12 is a diagram of a fluid moving through a conduit and illustrates a cell subject to a gradient of shear stress, with magnitude depending on its position relative to the axis of the conduit.

For calculating the minimum shear stress experienced by a given cell, the equation $\tau = \Delta Pr/2L$ was used, where $\Delta P$ is the change in pressure, r is the radius of the cell, and L is the length of the needle (1.27 cm). The assumption was made that cells were flowing along the axis of the needle in single file; thus keeping everything constant, the cell radius will determine the magnitude of shear force encountered.

Reynolds number was calculated to assume laminar flow using the equation $R_e = \rho v D/\eta$ where $\rho$ is the density of the culture media (0.998 g/cm$^3$), v is the velocity of flow, D is the diameter of the needle, and $\eta$ is the viscosity of the medium. For the 20 µL/sec (low) flow rate, $R_e$ is 159.58; for the 250 µL/sec (high) flow rate, $R_e$ is 1998. This indicates that all flow rates in the shear stress model were laminar.

Shear Stress Models 5 mL of a $5 \times 10^5$ cell/mL suspension was placed into 10 mL glass beaker (Pyrex) and loaded into a 5 mL syringe (BD Biosciences #309603) by slowly drawing the cells into the syringe manually. A 30 gauge needle (BD Biosciences #305106) was then attached to the syringe and cells were pushed through at a constant flow rate by one of two methods:

Syringe Pump:

A Harvard Apparatus PHD-2000 Infuse/Withdraw syringe pump was calibrated for the syringes being used and set to the appropriate flow rate (see Table I). After securing the syringe to the pump housing, a 6-inch small bore extension set (Smiths Medical MX448L) was used to connect the syringe and needle. The 10 mL beaker was secured at a 45-degree angle and the needle rested gently (without damaging the bevel) at the bottom of the beaker. The pump is then turned on and the cell suspension was collected into the beaker. The bore extension, still connected to the needle, was then removed from the syringe, and the syringe was removed from the pump. The cell suspension was re-loaded into the syringe as described above. In a standard assay, this process was repeated until cells have been passaged a total of ten times (control experiments were taken out to 15 passages). After each passage, 100 µL aliquots of cell suspension were removed from the glass beaker in duplicate for viability assays (described below). For non-shear stress treated control, cells which have been in suspension for the entire duration of the assay were aliquotted and treated as 100% viability controls.

250 µL/Sec Flow Rate:

This is the most commonly used flow rate throughout this example. To facilitate throughput, some experiments at 250 µL/sec were done manually. Here, cell suspensions were prepared as above with one exception: the small bore extension was not used, rather the needle was directly secured to the syringe. Suspensions were pushed through the needle by hand and collected into a 10 mL glass beaker. To control the flow rate using this approach, a timer was zeroed before each needle passage and the time taken to push a given volume through the needle was measured. At each passage, the volume in milliliters was divided by the time in seconds to give flow rate in mL/sec. Data for figures was only obtained from shear stress assays in which the average flow rate over 10 passages was ±10 µL/sec of the targeted 250 µL/sec. As data in FIG. 1 indicate, fluctuations within 10 µL/sec at this flow rate should not lead to significantly different viability results. Further, to assure reproducibility, most assays were repeated ten times or more.

Cell Viability Assays

Bioluminescence Imaging (BLI):

100 µL aliquots of shear stress-treated cells or control cells (those sitting in suspension through the duration of shear treatment) were loaded into a black 96 well plate (Costar) in duplicate. Each well was then diluted to 200 µL at final concentration of 150 µg/mL D-luciferin (Promega) using a multichannel pipette. Plates were incubated for 5 minutes at room temperature and then imaged for 5 minutes in an IVIS-100 (Xenogen). Bioluminescence measurements were collected using Living Image 2.50.1 software (Igor Pro). The photon flux of shear treated cells was divided by that of control cells to give % viability. All figures with BLI-derived viability data represent the average of at least 3 experiments.

WST-1 Viability Assay:

For primary cells and cell lines lacking luciferase-expression, cell viability was measured with (4-[3-(4-iodophenyl)-2-(4-nitrophenyl)-2H-5-tetrazolo]-1,3 benzene disulfonate (WST-1, Roche Applied Science) as directed. As indicated in FIGS. 1A-1D, WST-1 and BLI results were compared in parallel, showing agreement between the two methods.

Clonogenic Plating for Quantification of Cell Viability:

To support cell viability data acquired acutely using BLI and WST-1, clonal survival plating was performed. Here, 5 µL of a 1:10 dilution of control or shear stress-treated cells was plated into 10 cm plate in 10 mL of the appropriate complete culture media plus pen/strep. This volume contains an estimated 250 live cells prior to shear stress treatment ($5 \times 10^5$ cell/mL$\times 0.5 \times 10^{-4}$ mL=250 cells). Plates were incubated until visible colonies formed from single cells (depending on the cell line, this takes 1-2 weeks). Colonies were stained overnight with PBS containing 0.01% crystal violet and 0.02% citric acid, washed with distilled water, and counted on a light box. The number of colonies from shear treated suspensions was divided by that of control plates to give percent survival. Graphs derived using this approach represent the average of three experiments or more.

Flow Cytometry for Quantitative Analysis of Cell Viability:

This technique was used for leukocytes obtained from whole blood. Leukocytes, prepared as described above, were subjected to shear stress for ten passages. Before shearing and after each passage, 300 µL aliquots were placed in XXmL FACS tubes (BD Biosciences) in duplicate. 100 µL of DMEM containing $1 \times 10^6$ counting beads/mL (Caltag Laboratories) was added to each tube, as well as propidium iodide to a final concentration of 0.5 µg/mL. Single cells were gated on forward and side scatter, on a BectonDickenson LSR. Stop gates were set to 5,000 counting beads to assure consistency across samples. The ratio of live (propidium iodide-negative, calcein-AM-positive) cells to counting beads at each passage was compared to non-shear stress-treated controls to provide percent viability.

Flow Cytometry Analysis of Propidium Iodide Uptake

200 µL of cell solution was taken for each sample and added to 200 µL of complete culture medium in 5 mL polystyrene FACS tubes (BD Biosciences). Propidium iodide (final concentration of 0.5 µg/mL) was added either before the first, sixth, eighth, or tenth shear passages. Cells were analyzed on a BectonDickenson LSR with Violet. Single cells were gated by forward and side scatter, consistent with viability, and evaluated for PI and/or Calcein AM positivity.

Statistical Analyses

For statistical analysis of cell size and endpoint shear stress survival, paired 2-tailed t-tests were used when comparing two cell lines or flow rates. When comparing the endpoint survival of three or more cell lines or flow rates, one-way ANOVA followed by Bonferroni post tests were performed. When comparing shear stress survival of multiple cell lines over repeated passages, repeated measures ANOVA followed by Bonferroni post tests were used.

Results

In Vitro Model of Fluid Shear Stress Induces Cell Death in a Dose-Dependent Fashion.

To directly test the effect of fluid shear stress on cancer cells, an experimental protocol involving the repeated passage of cell suspensions through a 30 gauge needle (150 μm internal diameter) was used. By holding a constant flow rate, the magnitude shear stress experienced at the wall of the needle was controlled. Changes in cell viability resulting from exposure to shear stress were closely monitored throughout the protocol using bioluminescence imaging (BLI). The range of wall shear stress targeted in the protocol (Table 1) encompassed high physiological values estimated in the human vasculature, and beyond [Reneman, R. S. and A. P. Hoeks, Wall shear stress as measured in vivo: consequences for the design of the arterial system. Med Biol Eng Comput, 2008. 46(5): p. 499-507., Schneider, S. W., et al., Shear-induced unfolding triggers adhesion of von Willebrand factor fibers. Proc Natl Acad Sci USA, 2007. 104(19): p. 7899-903.]. Using a Coulter Counter, the mean cell radius of PC-3 was determined to be 9.3 μm. Applying the shear stress equation, this radius was used to estimate the minimal (axial) shear forces PC-3 cells encounter in this model. These values are shown for each flow rate in Table 1.

| Flow Rate (μL/sec) | Wall Shear Stress (dyn/cm2) | Minimum Shear Stress (dyn/cm2) | Time of passage (msec) |
|---|---|---|---|
| 20 | 509 | 59.53 | 12.2 |
| 35 | 890 | 104.09 | 6.97 |
| 50 | 1,271 | 148.65 | 4.88 |
| 100 | 2,543 | 297.43 | 2.44 |
| 150 | 3,815 | 446.20 | 1.62 |
| 250 | 6,358 | 743.63 | 0.89 |

Figure 7:
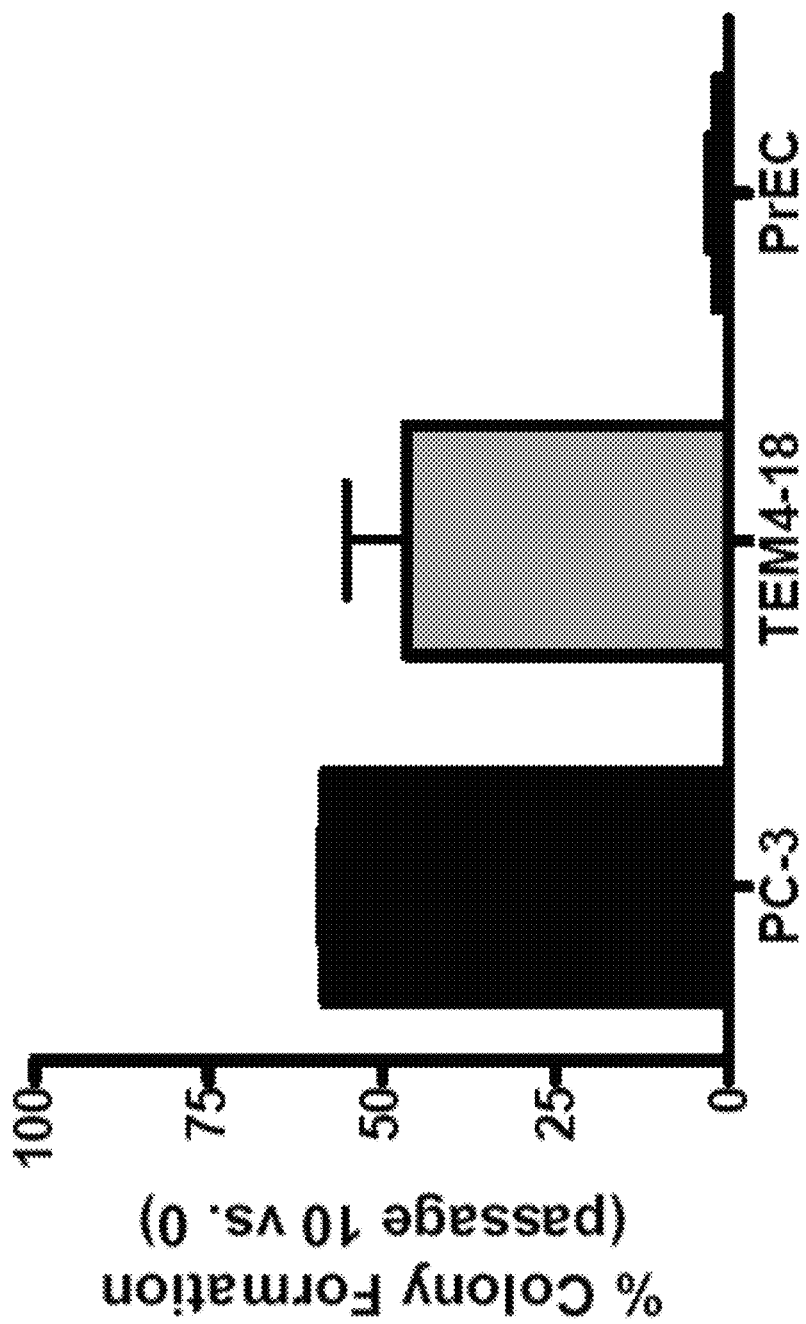
FIG. 7: Clonogenic survival correlates with bioluminescence imaging viability data. PC-3, TEM4-18, and PrEC cells which had been subjected to 0, 2, or 10 passages at 250 µL/sec ($6.36 \times 10^3$ dyn/cm$^2$) were plated at clonal density. Colonies resulting from live, single cells were stained and scored. Data shown on graph is the average of three independent shear treatments and subsequent plating assays. This data correlates well with viability data derived via bioluminescence imaging. n=3 for each condition, done using manual method.

Using this protocol, the survival of the human prostatic carcinoma cell line, PC-3, was analyzed after 10 passages of fluid shear stress (FIG. 1A) and revealed a dose-dependent sensitivity of these cells to shear stress. When analyzing the survival curves of PC-3 cells over repeated shear stress passages (FIG. 1B) little loss of viability was observed at the lowest flow rate and a biphasic loss of viability at the highest flow rate. The cell viability measurements acquired with BLI were confirmed by using other techniques to assess cell viability following the shear stress protocol. A WST-1 assay of mitochondrial function as well as clonogenic survival of control and shear stress-treated PC-3 cells were performed. Results from these other methods mirrored acute changes in viability measurements obtained using BLI (FIG. 1C). FIG. 7 shows a comparison of PC-3 clonogenic plating with cells used in later figures.

Since shear force experienced by individual cells in this experiment could be influenced by neighboring cells in suspension, PC-3 survival over a 10-fold range of cell concentration was evaluated. It was shown that shear stress induced cell death was not affected by cell concentrations between $5 \times 10^4$ and $5 \times 10^5$ cells/mL (FIG. 1D). Whether cell viability in the shear stress protocol is influenced by the confluence (growth phase) of cells prior to suspension was also investigated. PC-3 cells were trypsinized at low and medium confluence, as well as those which had just reached full confluence (but not over-grown) and similar shear stress survival was found (FIG. 1D). To show that cell viability was not affected by material released by damaged or dead cells, fresh cells were suspended in cell-cleared medium from shear stress-treated cells. Cell viability of these suspensions was not different than cells in fresh media after 10 passages at 250 μL/sec (FIG. 1D). In addition, it was shown that the viability of cells in the protocol was similar between those collected by trypsin and versene (non-enzymatic) treatment (FIG. 1D). Finally, conditions tested included needle length (FIG. 1D). Only under this final condition, where the time of exposure to FSS was effectively doubled, was a significant difference in endpoint survival noted. (*$p<0.05$ vs all other conditions, one-way ANOVA, followed by Bonferroni's post test. All experiments n=4 using pump method.)

Collectively, these data show that loss of cell viability increases proportionally with the magnitude of shear stress in a manner independent of cell culture and suspension preparation.

Figure 1C:
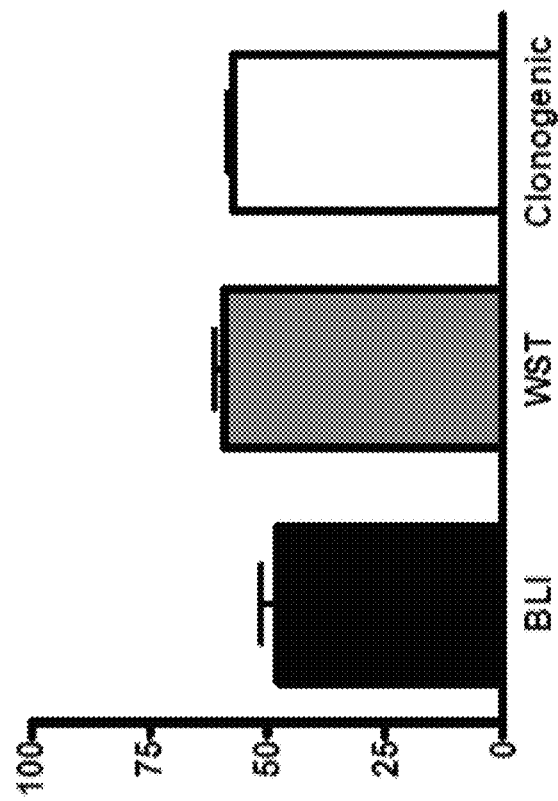
Figure 1D:
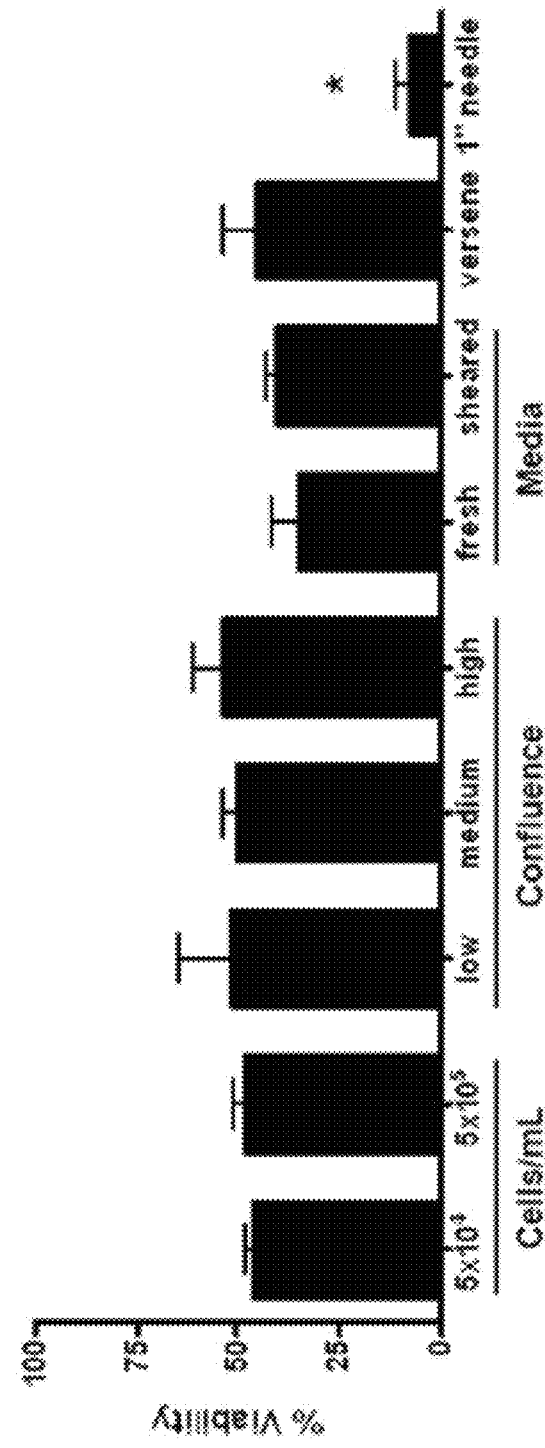
Figure 8:
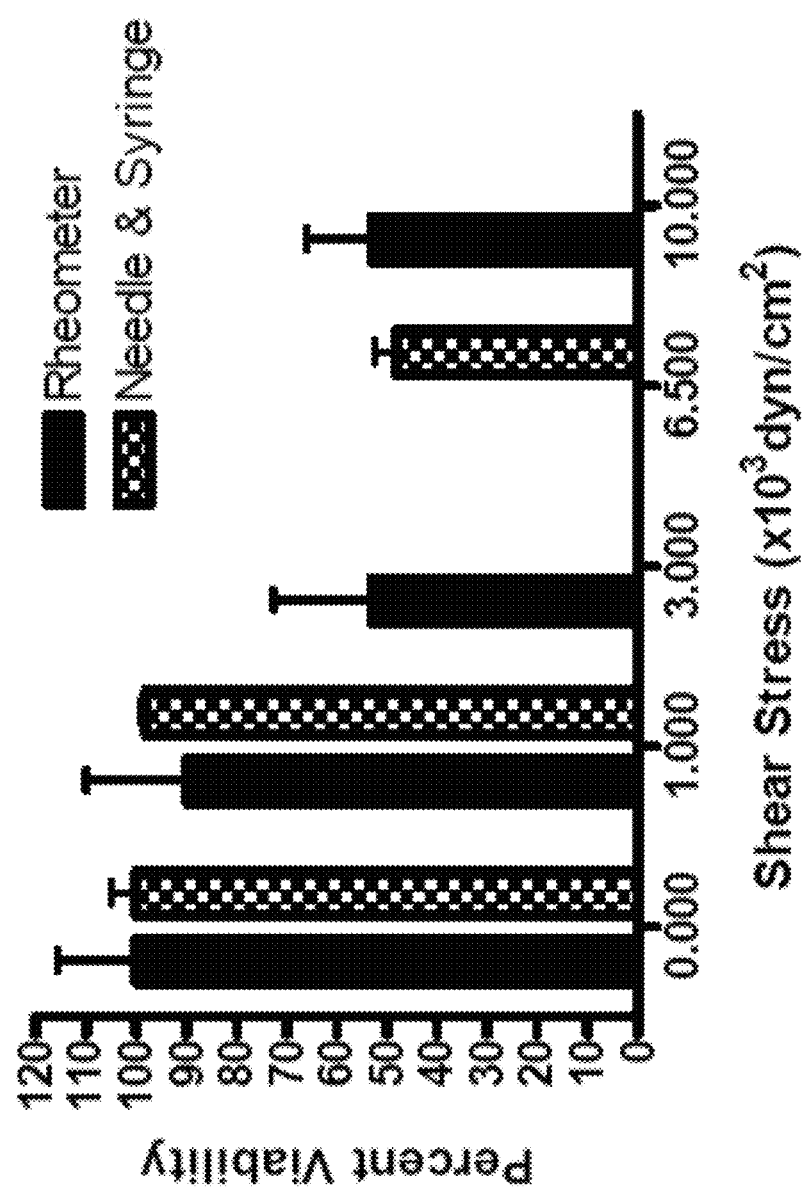
FIG. 8: Comparison of cancer cell death under needle and syringe and rheometer fluid shear stress techniques. PC-3 cell viability data shown in FIG. 1A (checkered bars) is compared to PC-3 cells treated at escalating doses of shear stress using a rheometer. All data were acquired using BLI and rheometer experiments were done three times.

To help validate the model, the viability of cells in FIG. 1A were compared to PC-3 cells subjected to short pulses of shear force using a rheometer. Over a range of shear stress magnitudes, this approach caused a similar amount of cell death as our needle and syringe system (FIG. 8).

Figure 2A:
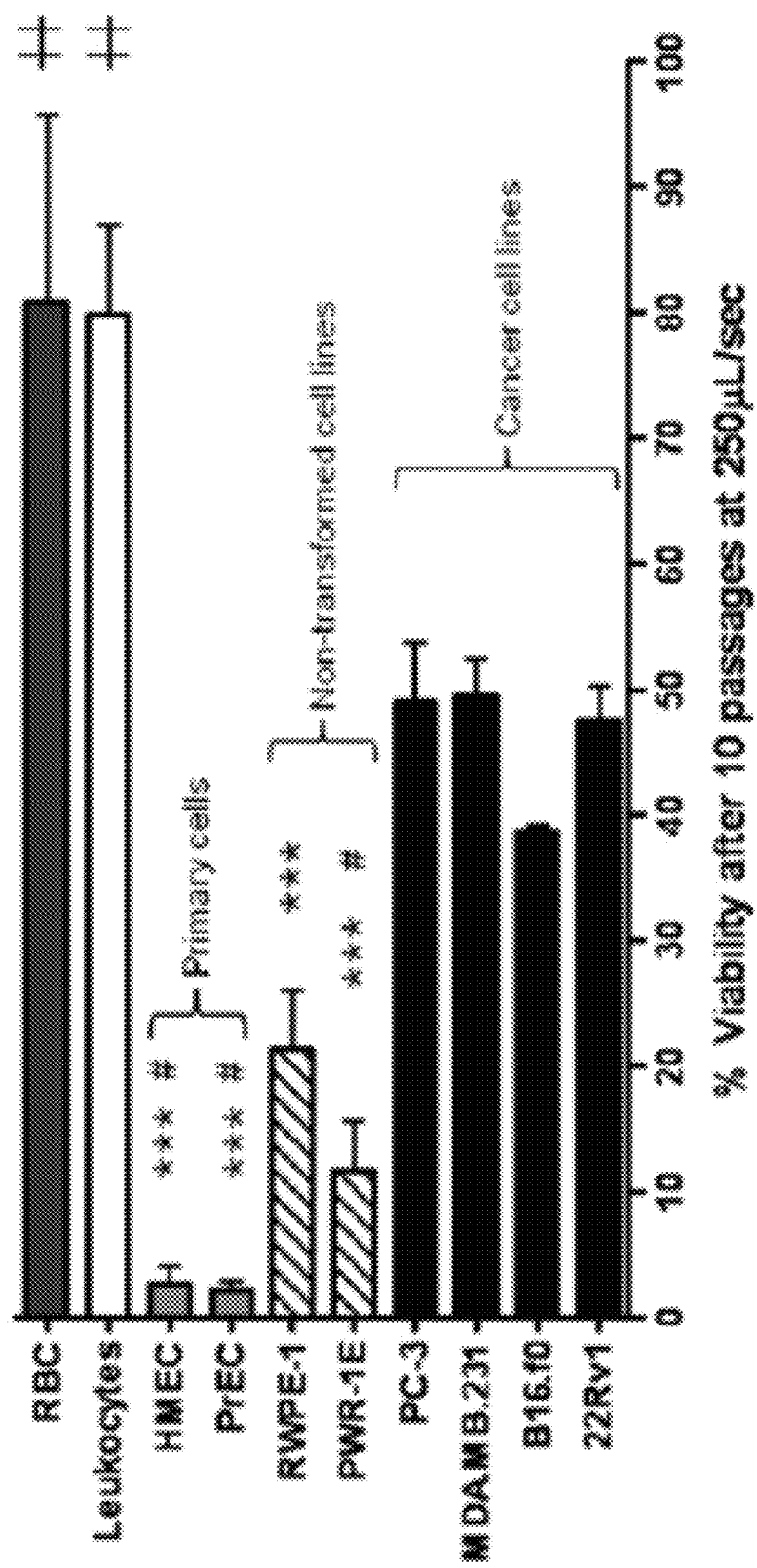
FIGS. 2A-2D show that carcinoma cells of various histological origins exhibit unique resistance to fluid shear stress.
Figure 2B:
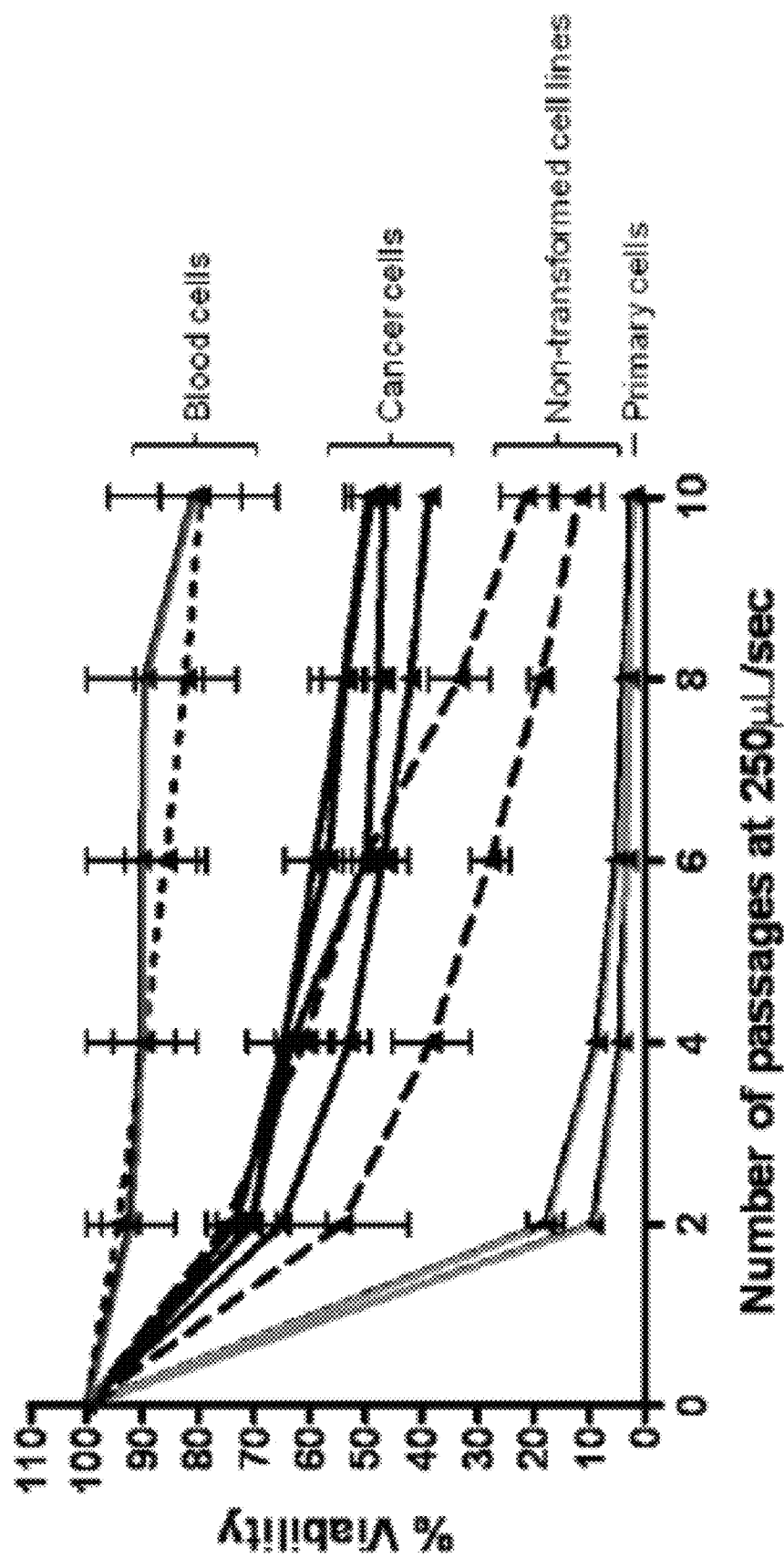

Carcinoma Cells of Various Histological Origins Exhibit Unique Resistance to Fluid Shear Stress Next, the shear stress protocol was employed to test for differences in survival between carcinoma cell lines derived from metastatic prostate (PC-3 and 22Rv1), breast (MDA.MB.231), and melanoma (B16f0). Surprisingly, only small, insignificant differences in the survival of these cancer cell lines at the 250 μL/sec flow rate (black bars in FIG. 2A and FIG. 2B) was observed. Also included in this analysis were two immortalized, but non-transformed cell lines of the human prostate (PWR-1E and RWPE-1) as well as primary cells of the human breast and prostate (HMEC and PrEC, respectively). Much greater cell deaths were measured in these epithelial cell types versus all cancer cell lines (FIG. 2A and FIG. 2B). Freshly isolated mouse red blood cells (RBCs), on the other hand, are robustly resistant to this level of shear stress (FIG. 2A and FIG. 2B). Similarly, freshly isolated human leukocytes also display great resistance to shear forces (FIG. 2A and FIG. 2B). This finding underscores the unexpected ability of these transformed epithelial cells to survive these magnitudes of shear stress.

Figure 2C:
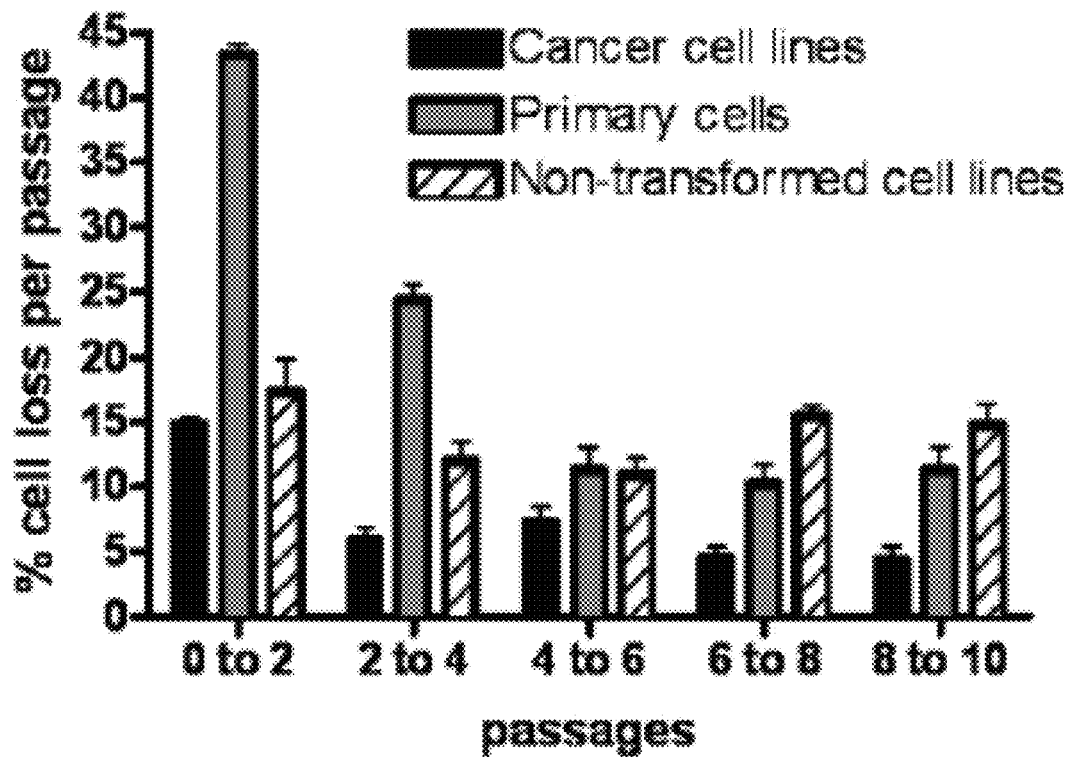

As mentioned above, PC-3 cells exhibited a biphasic survival curve at flow rates above 20 μL/sec. Impressively, a very similar shape was observed for the survival curves of the other cancer cell lines tested. Meanwhile, cell death in the immortalized, but non-transformed cell lines was much more linear. Although the survival curves of primary cells also appear biphasic, nearly 90% of all cells in suspension had died by the second passage of shear stress, compared to an average of only 30% of cancer cells (FIG. 2B). The percentage of cell loss per passage of shear stress is shown graphically in FIG. 2C.

Figure 2D:
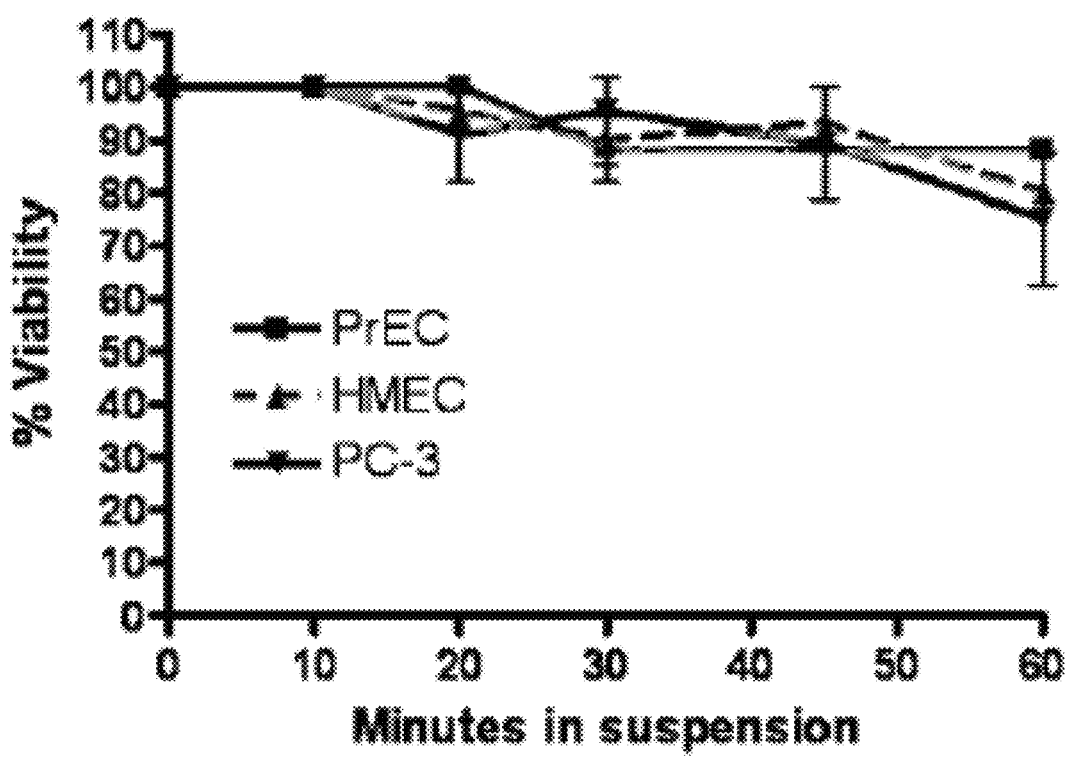

Resistance to detachment-induced cell death, or anoikis, is a hallmark of cancer. Therefore, the viability of non-shear stress-treated PC-3 cells was compared to the viability of non-transformed cell lines and primary cells over a one hour period in suspension. The viability of all cells tested was unaffected by detachment within 10 minutes in suspension and there was only a small amount of cell death during a 30 minute period, which is the time that it takes to perform the shear stress protocol at the lowest flow rate, which represents the longest assay flow rate (FIG. 2D). Therefore, differences in shear stress survival between these cell types are not likely due to exacerbations in detachment-induced cell death.

Figure 9:
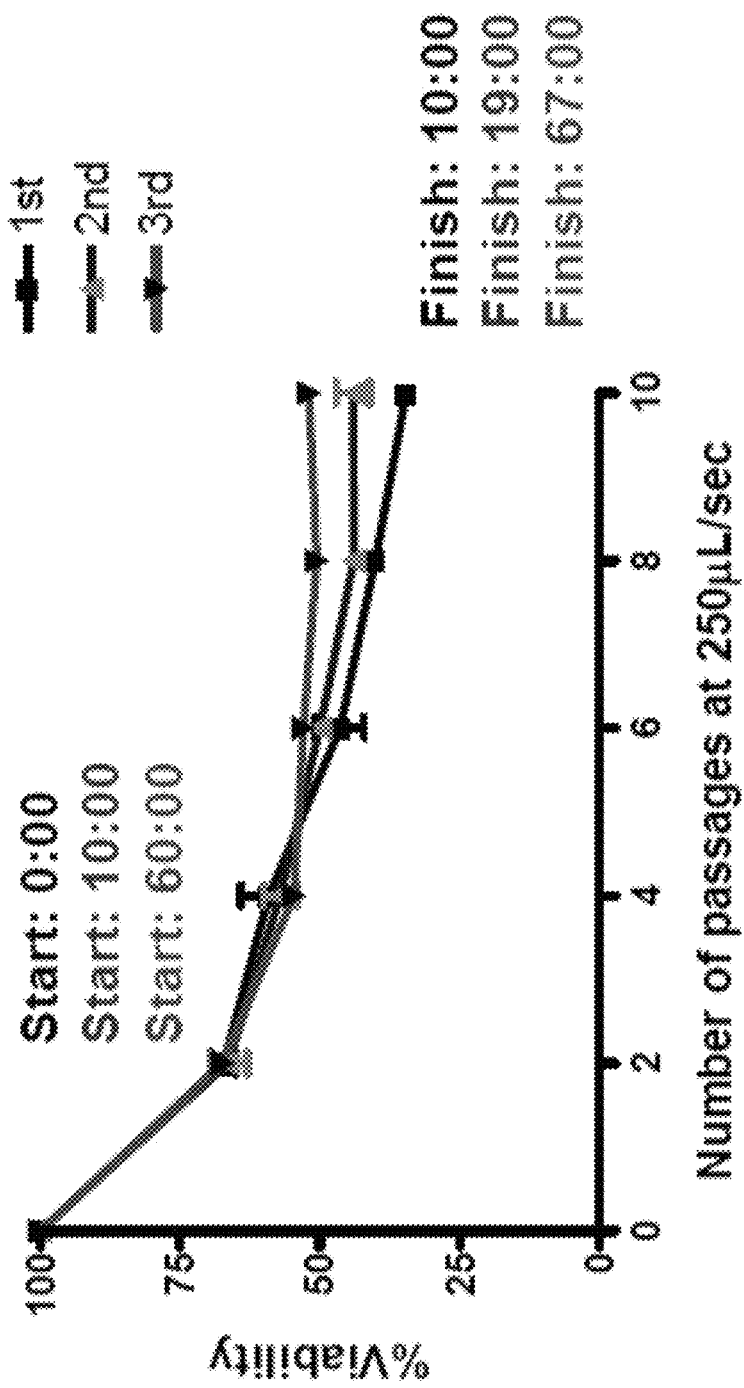
FIG. 9: Response of PC-3 cells to shear stress is similar over a range of time post-suspension. An aliquot of freshly suspended PC-3 cells was analyzed for shear stress survival (1'). Once this first protocol was finished, another aliquot of the PC-3 stock was subjected to the protocol ($2^{nd}$). One hour after suspension, a final round of shear protocol was performed ($3^{rd}$). Regardless of time since preparing the cell suspension, the response of PC-3 cells to shear stress was similar. Survival is represented as percent viability of non-shear treated cells which are held in suspension for the duration of the assay (for each time period post suspension, n=3 using manual method).

Whether the biphasic survival response of cancer cells was dependent upon changes which occur in freshly suspended cells was also investigated. A suspension of PC-3 cells was made and divided it into three aliquots; shear treatment was started as usual using the first aliquot. The next was sheared following the initial round, which took roughly 10 minutes. The third aliquot was held for one hour before shearing. Viability data for each aliquot was similar (FIG. 9).

Figure 10A:
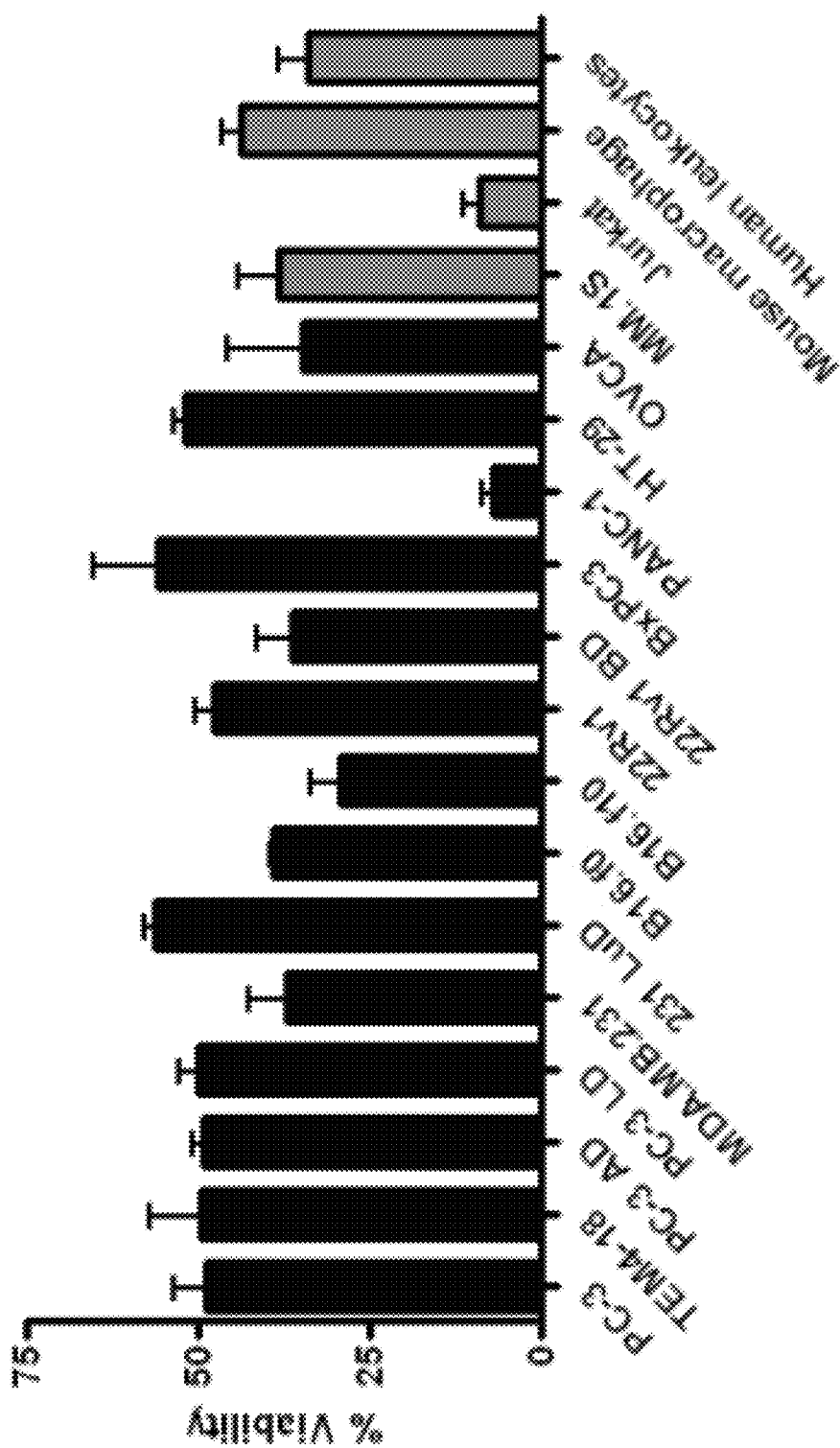
FIGS. 10A-10B show shear stress analysis of a broad panel of cells. Cancer cells derived from various epithelial tissues, as well as hematogenous origin were analyzed for survival over ten passages of shear stress at 250 µL/sec.
Figure 10B:
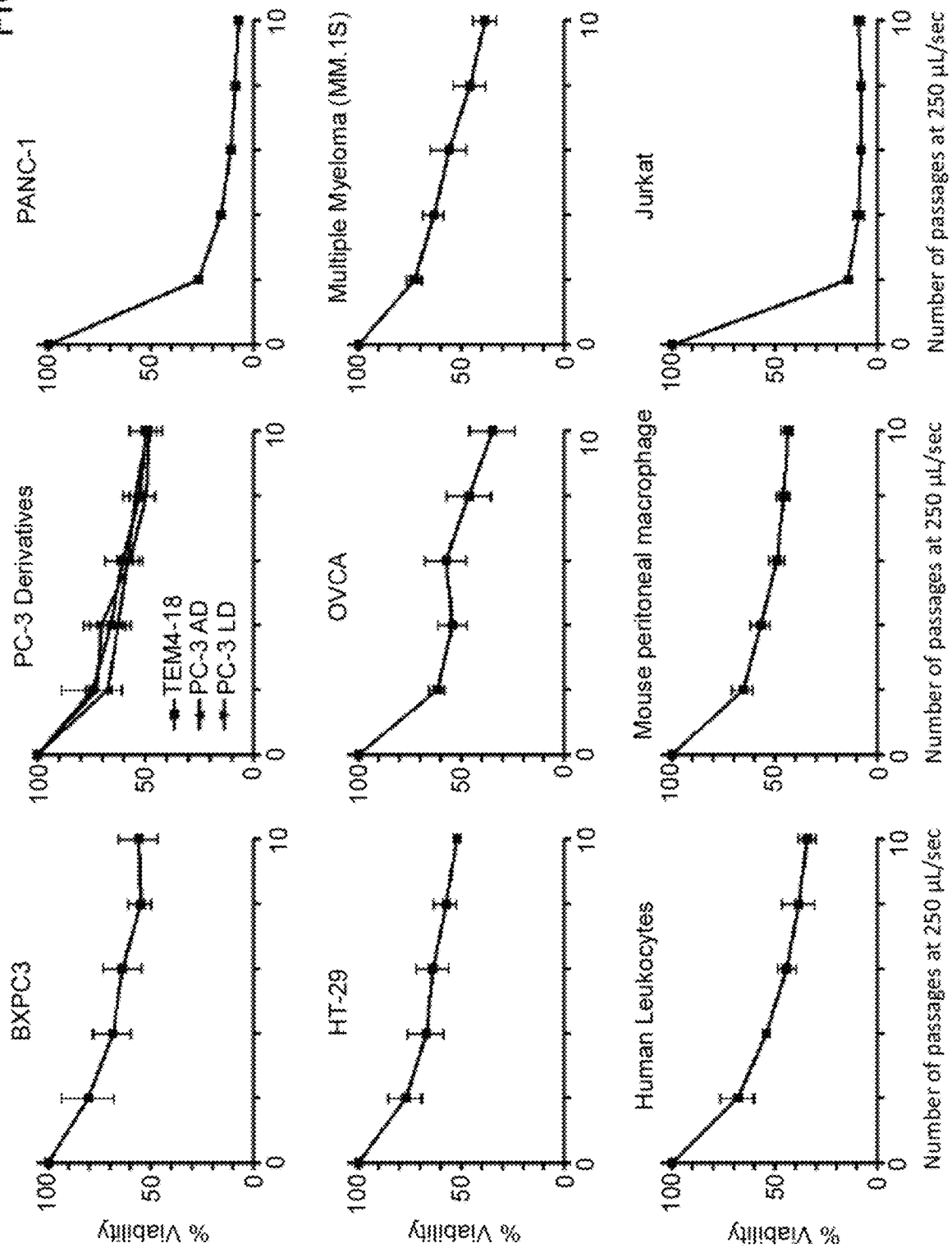

Finally, it is known that serial passage of human or mouse cancer cell lines through mice via systemic injection often selects for cells that exhibit enhanced metastatic potential [Fidler, I. J., Biological behavior of malignant melanoma cells correlated to their survival in vivo. Cancer Res, 1975. 35(1): p. 218-24., Fidler, I. J. and M. L. Kripke, Metastasis results from preexisting variant cells within a malignant tumor. Science, 1977. 197(4306): p. 893-5.]. Therefore, the possibility that experimental metastasis selects for cells of increased shear stress resistance was tested by comparing the survival of PC-3, MDA.MB.231, and B1610 cells with their in vivo derivatives in the shear stress protocol. No appreciable differences in shear stress resistance between parent cancer cells versus metastatic derivatives (showed alongside many other cell lines in FIGS. 10A-10B) was detected. This finding suggests that metastasis does not select for shear stress resistance, however we note that PC-3 and MDA.231 are both derived from metastatic tumors, thus these cells have previously experienced circulation prior to passage in mice.

Shear Stress Resistance in Carcinoma Cells is Transient and Inducible

Figure 3:
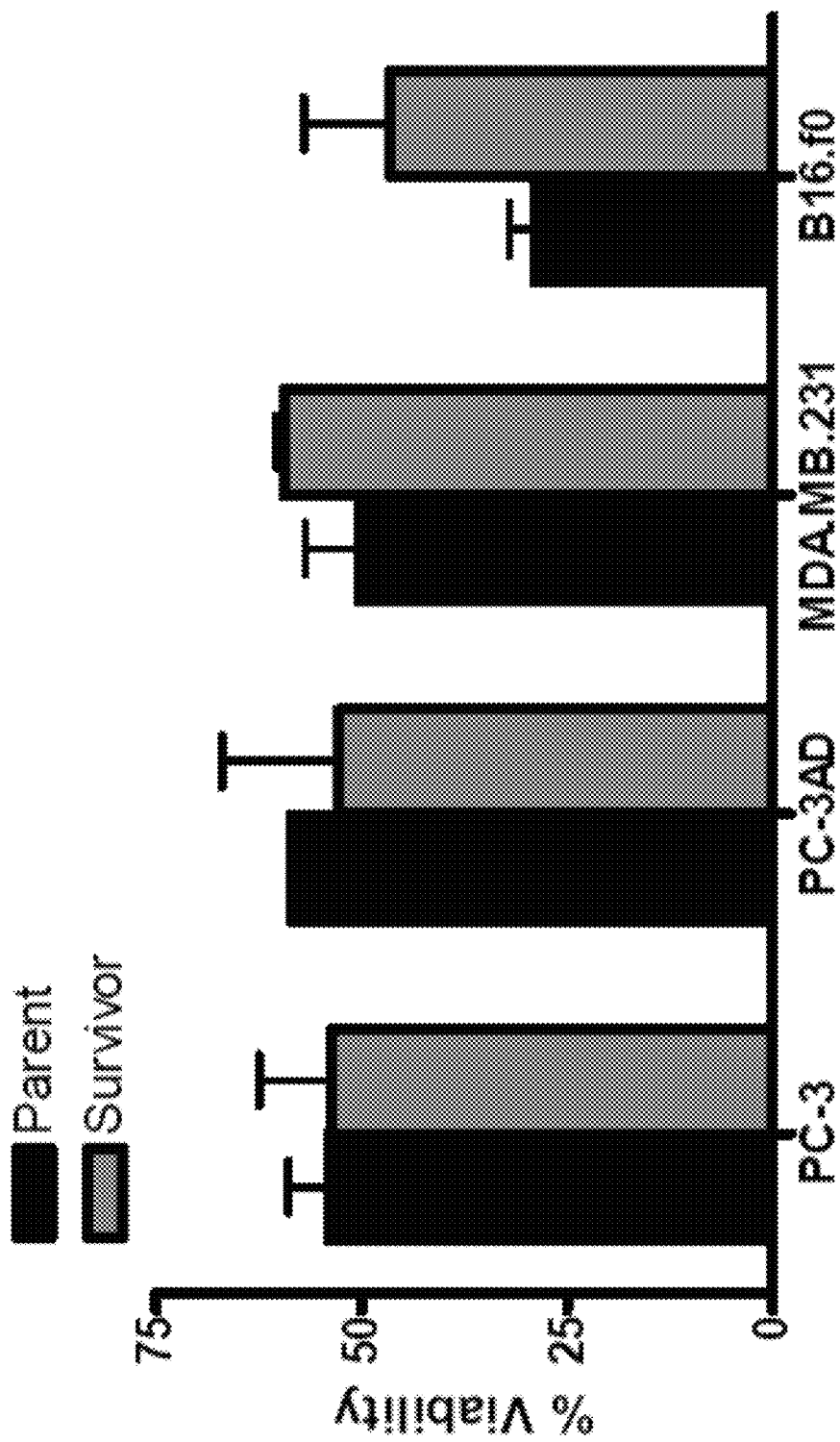
FIG. 3 shows shear stress resistance in carcinoma cells is transient and inducible. After 10 passages of fluid shear stress at 250 µL/sec, surviving PC-C, PC-3 adrenal gland-derivative, and B1610 cells were allowed to recover in culture for 24-48 hours. These survivors were then compared for shear stress resistance in parallel with the corresponding shear stress-naïve control cells. Subculturing surviving cells did not enrich for shear stress resistance at 250 µL/sec (no significant differences by one-way ANOVA, n=3 for each cell line using manual method).

The observation that cancer cell death was precipitous over the first two passages of the shear stress protocol, but diminished with subsequent passage led to the hypothesis that passage selects for shear stress-resistant subpopulations within the cancer cell lines. If this resistance phenotype has a genetic basis, then cells collected following the shear protocol should exhibit enhanced resistance to shear stress. However, this was not found to be the case. In several cell lines, exposing shear stress-surviving cells to a second round of shear protocol after recovery in culture demonstrated that survival was similar to the initial round of the shear protocol (FIG. 3). This data supports the conclusion that the dramatic reduction in the rate of cell death observed in cancer cell lines results from a transient, physiologic protective response to shear stress.

Figure 4A:
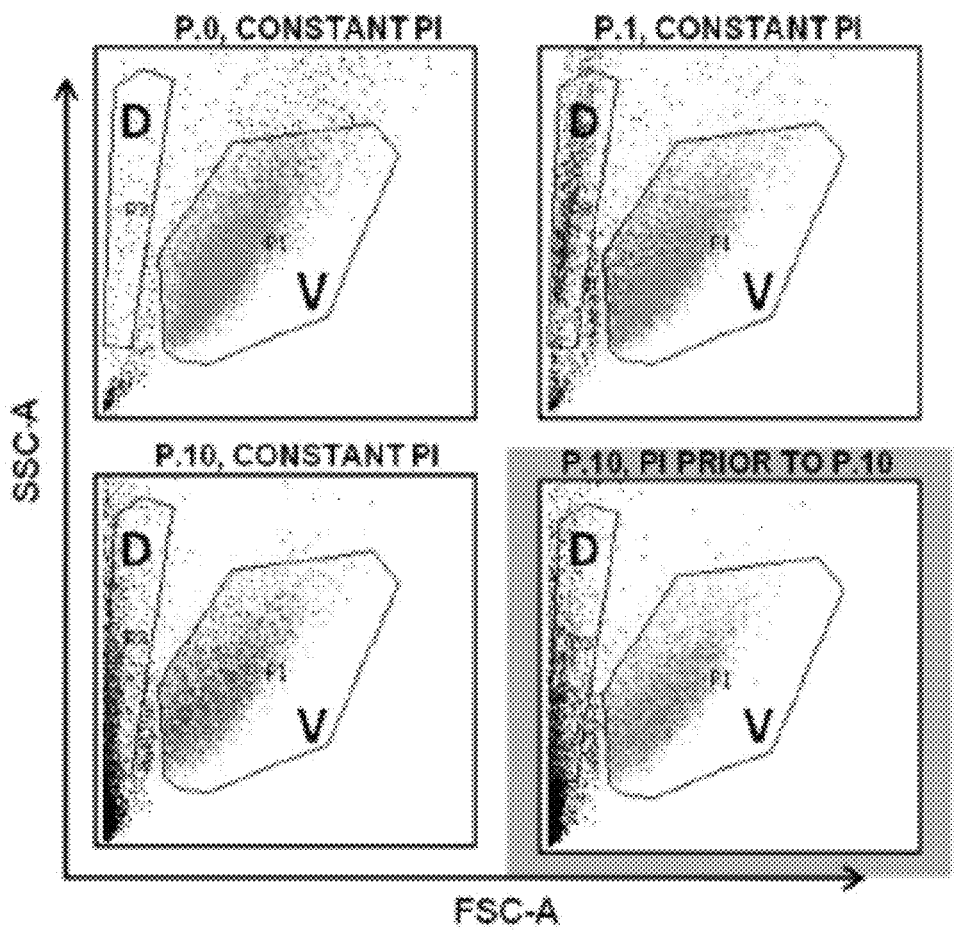
FIGS. 4A-4D show that selective and diminishing accumulation of membrane-impermeable dye in PC-3 cells exposed to shear stress reflects changes in cellular membrane integrity and induced resistance to shear forces. PC-3 cells subjected to shear stress in the presence or absence of propidium iodide (PI) were collected after each passage for flow cytometric analysis. PI was added to the cell suspension either prior to shear passage 1 (p1), 6 (p6), 8 (p8), or 10 (p10). Viable cells (P1+P2 gated), defined by cell size, shape, and density (forward scatter and side scatter), were evaluated for PI positivity. When exposed to PI constantly (FIG. 4A, upper right), p1 resulted in 7.28% of the population of viable cells accumulating PI intracellularly, as compared to non-sheared cells (0.65%, FIG. 4A, upper left). With sequential shearing, the p10 sample resulted in a final accumulation of PI in 36.73% in the viable cell population (FIG. 4A, lower left). In contrast, when PI was introduced to the cells prior to p10 (FIG. 4A, lower right), only 4.22% of the cell population accumulated PI.
Figure 4B:
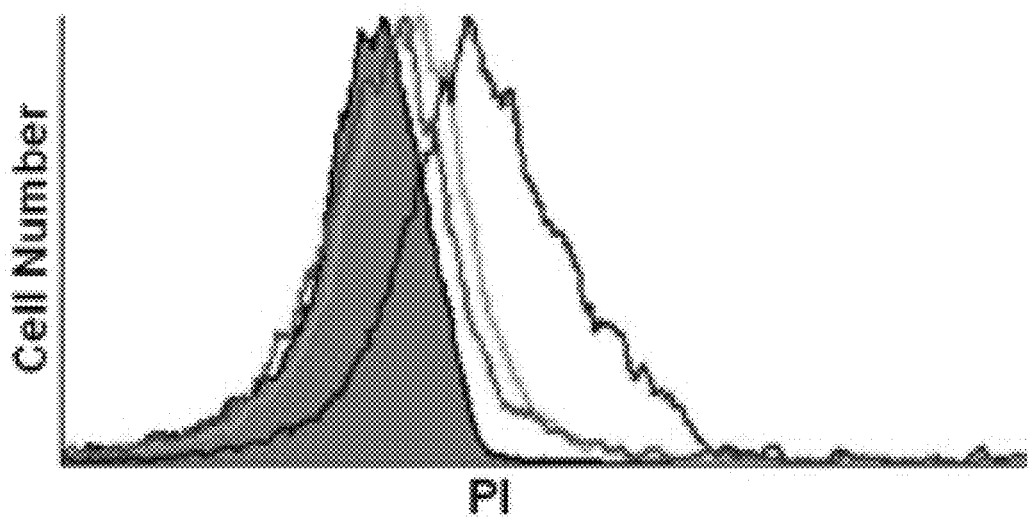

Repeated Exposure to Shear Stress Results in Changes in Cellular Membrane Integrity and Induced Resistance to Shear Forces The observation of a biphasic viability curve in cells sheared at greater than 20 μl/sec led to the hypothesis that cancer cells exposed to shear forces can elaborate changes conferring greater resistance to future shear forces, and thereby resist death by avoiding irreparable membrane damage. Implicit in the hypothesis was the ability of cells to repair a certain degree of membrane damage. To address this hypothesis, the shear protocol was conducted in the presence of propidium iodide (PI). Typically used to mark non-viable cells by virtue of its membrane-impermeability, the accumulation of PI within viable cells was evaluated to represent a cell population that sustained and repaired membrane damage secondary to shear forces. Before the first, and after each subsequent passage, an aliquot of cell suspension was removed for FACS analysis. When analyzing cell suspensions for PI positive cells within a gate consistent with viability by forward and side scatter parameters, viable non-sheared PC-3 cells demonstrated minimal PI accumulation (mean 0.65% of viable cells, n=9, FIG. 4A, upper left). After an initial shear passage, PI accumulated in 7.28% of the viable cell population (FIG. 4A, upper right). With continuing passages, more PI accumulated, ultimately maximized after passage 10 with 36.73% of viable cells displaying positive staining (FIG. 4A lower left). This data indicates that previously undamaged cells sustain membrane damage sufficient to allow PI uptake over repeated passages.

Figure 4C:
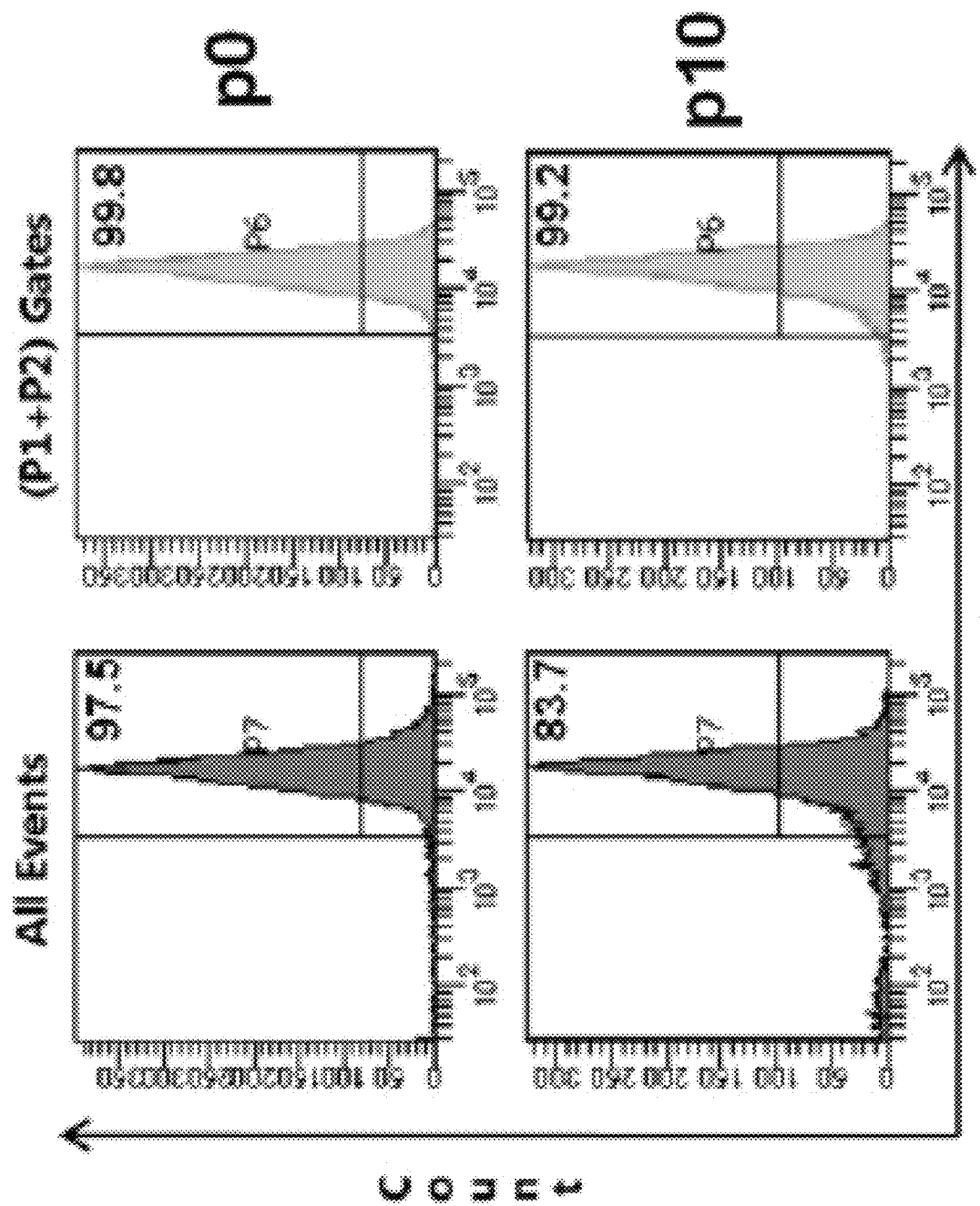

To confirm cell viability as gated by forward and side scatter gates, the vital stain, Calcein AM, was employed. Both prior to shearing and after 10 passages, nearly all of the cells in the gate of interest were Calcein AM positive (99.8% and 99.2%, respectively), confirming that all of the cells in gates P1+P2 were, indeed, viable (FIG. 4C).

Figure 4D:
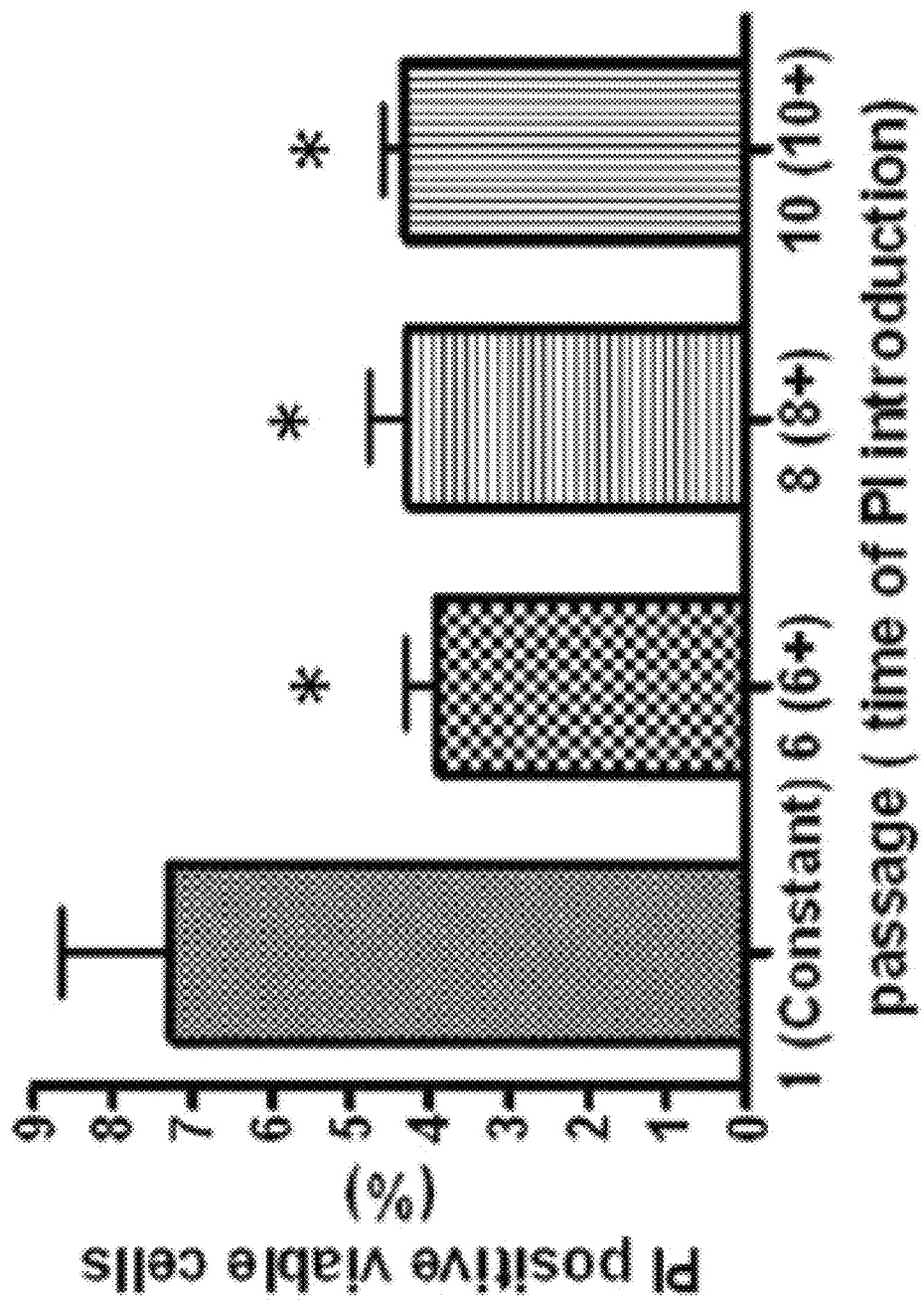

When PI was withheld from cell suspension until after passage 9, less uptake of the dye into sheared cells was observed than was observed after passage 1 in constant presence of PI (4.22% versus 7.28%, respectively; FIG. 4A, lower right vs. FIG. 4A, upper right). When plotted over repeated passages in constant presence of PI, there was less PI accumulation per passage, on average, in the intervals from passage 3-6 and 7-10 (3.25% and 2.92%, respectively) than in the first passage alone (6.64%). The gradual diminution of additional PI accumulation suggests that fewer cells were being damaged sufficiently to allow PI uptake, reflecting a smaller population eligible for membrane-damaging destruction. If this assumption is true, introduction of PI to cell suspensions at points intermediate in the assay would be expected to reveal less PI accumulation than observed when PI is added prior to passage one. In FIG. 4D, PI was added either prior to passage 1, 6, 8, or 10, and then sheared to completion (10 passages). Regardless of when PI was added, the first passage in its presence elicited a pronounced increase in PI positivity; however, this increase was significantly less than that seen at passage 1 in constant presence of PI (7.28%+/-1.38% versus 3.62% p6, 4.90% p8, and 4.22% p10). Because the FACS analysis was performed on an equal number of viable cells at each passage, cell death was not responsible for the diminution of PI accumulation. Rather, these data suggest that during flow, PC-3 cells in the model experience a range of shear forces; some sufficient to alter the membrane integrity of a cell, but insufficient to cause irreparable membrane damage. The reduced uptake of PI into cells over later passages suggests that PC-3 cells can evoke an induced response that results in raising the threshold for both reparable membrane damage as well as irreversible, lethal damage.

Induced Shear Stress Resistance Requires Extracellular Calcium

Figure 5A:
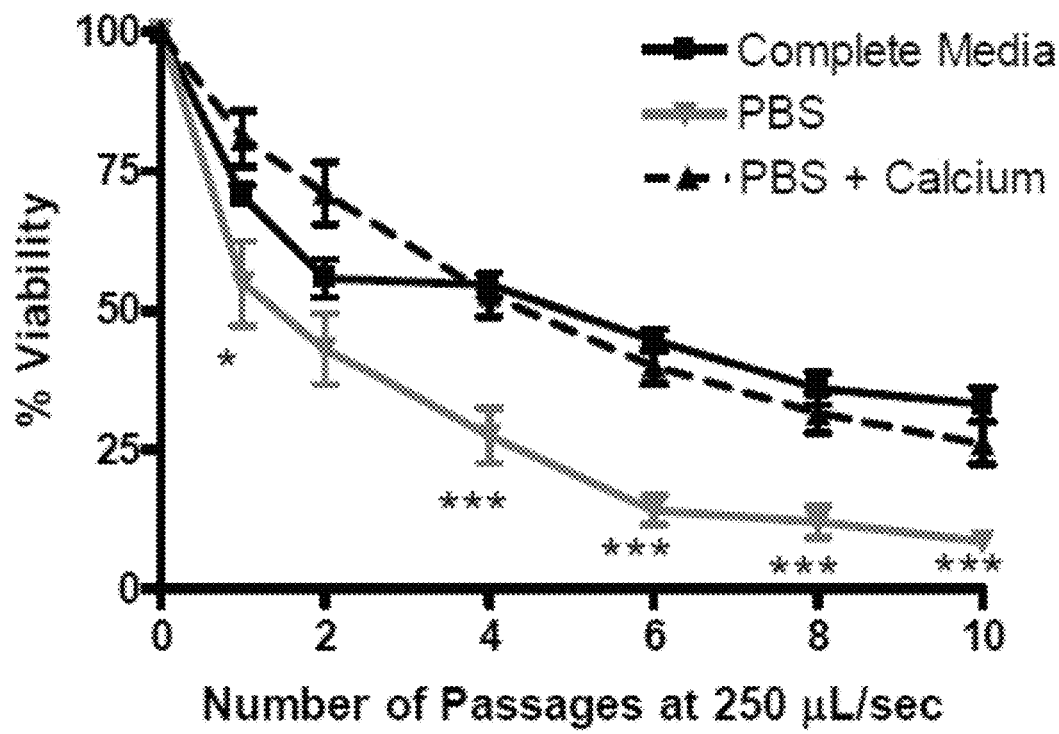
FIGS. 5A-5B show that shear stress-induced cancer cell membrane repair requires presence of extracellular calcium.

Mechanical damage to plasma membranes can be repaired, in certain cell types, by a fusion of vesicles in a mechanism that requires the influx of extracellular calcium [Bement, W. M., et al., Rehabilitation and the single cell. Curr Opin Cell Biol, 2007. 19(1): p. 95-100.]. This healing process has been reported to require the activity of Rho-GTPases and actin polymerization at the site of the wound [Terasaki, M., K. Miyake, and P. L. McNeil, Large plasma membrane disruptions are rapidly resealed by Ca2+-dependent vesicle-vesicle fusion events. J Cell Biol, 1997. 139(1): p. 63-74.]. Therefore, whether the observed shear stress survival response in cancer cells also requires extracellular calcium was investigated. When PC-3 cells were suspended in nominally calcium-free PBS and subjected to the shear stress protocol, a more steady loss of cell viability and an 8-fold increase in total cell death was observed (FIG. 5A). When suspensions of cells in PBS are supplemented with calcium at the same concentration as complete tissue culture medium a survival curve not significantly different from the media control suspensions was observed (FIG. 5A). These data suggest that shear stress damage to cancer cells triggers a survival response which requires extracellular calcium.

Figure 5B:
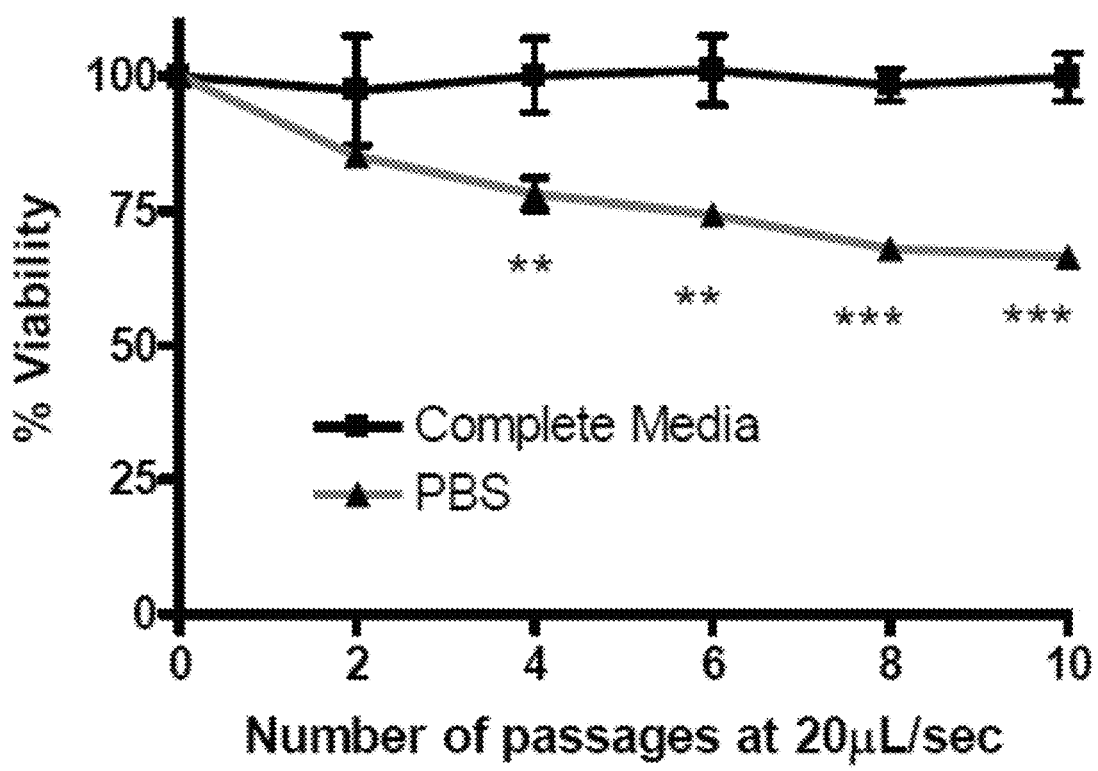
Figure 11:
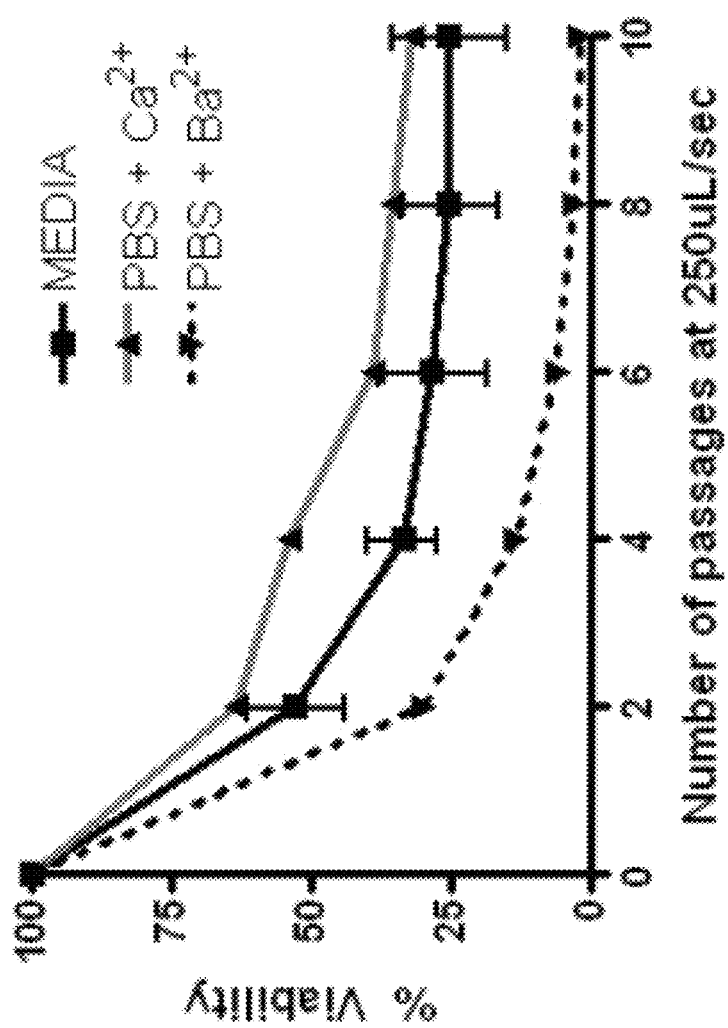
FIG. 11: Shear stress resistance response specifically requires calcium. PC-3 cells suspended in complete medium, calcium-free PBS, or PBS plus either calcium, magnesium, or barium (88 mM final concentration, respectively) were subjected to shear stress at 250 µL/sec. In PBS, shear stress induced is greatly enhanced. Only addition of calcium to PBS rescues the shear stress resistance phenotype. Currently, n=1 for each condition using syringe pump.

In complete medium, PC-3 cells exhibit little cell death at the 20 µL/sec flow rate (as seen in FIGS. 1A-1D). However, when subjected to this flow rate in calcium-free PBS, these cells exhibit a linear loss of viability with roughly 35% more cell death than in the presence of calcium (FIG. 5B). This finding indicates that the protective shear stress survival response can be triggered at lower magnitudes of shear force, which may be more commonly encountered physiologically by CTCs. Finally, to test the specific requirement of calcium in this shear-induced survival response, it was shown that cells suspended in PBS supplemented with barium were equally susceptible to shear stress as cells in nominally calcium-free PBS (FIG. 11).

Induced Shear Stress Resistance Requires Actin Polymerization

Figure 6A:
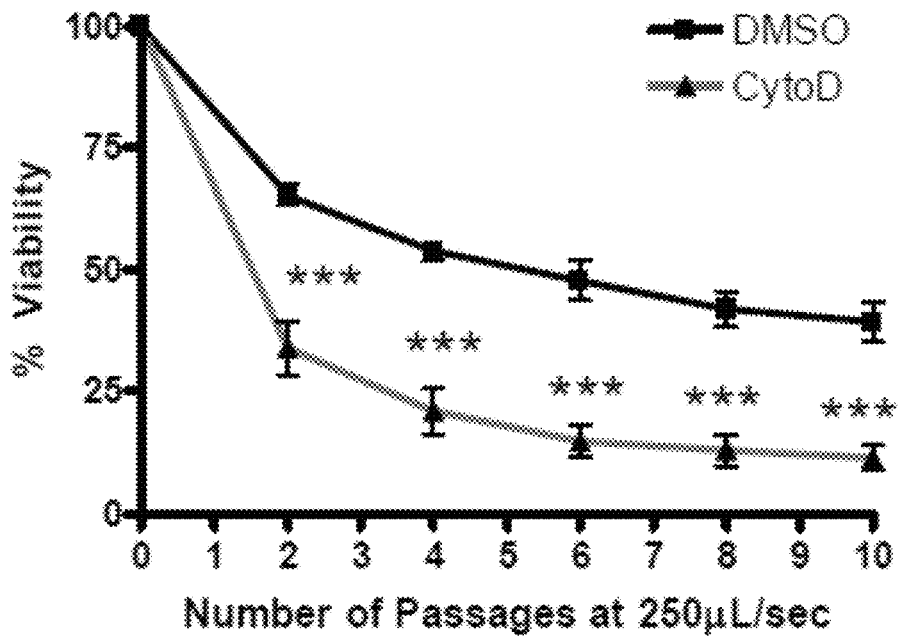
FIGS. 6A-6B show that induced shear stress resistance requires actin polymerization.
Figure 6B:
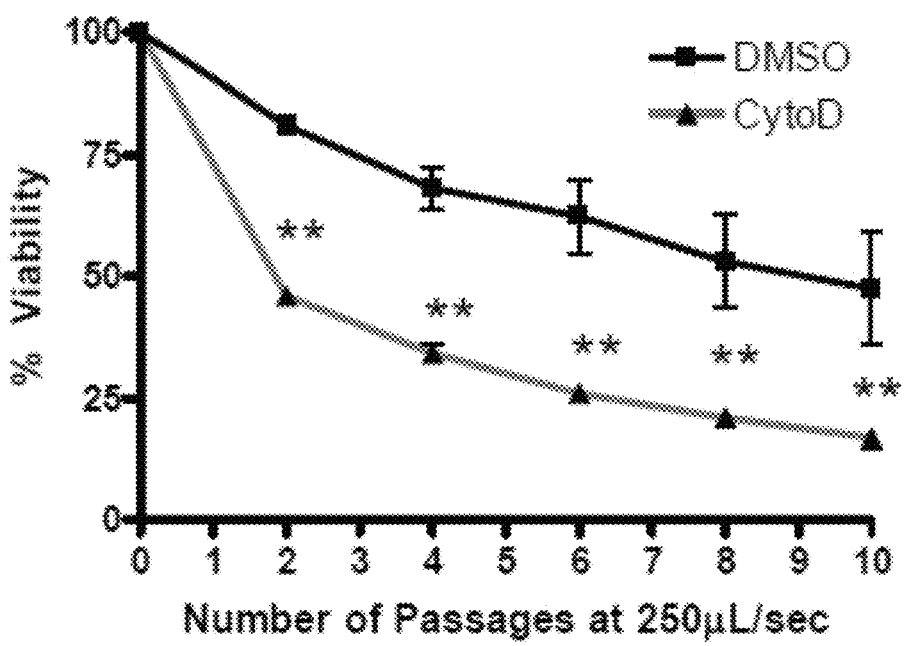

Next, whether rearrangements of the cytoskeleton occur in response to shear stress and thereby imparts a protective advantage to cells was investigated. In support of an active biological process, it was found that cell suspensions which were held on ice, and thus expected to have reduced signaling kinetics, for 20 minutes prior to the shear protocol exhibited significantly greater loss of cell viability than under usual conditions (data not shown). To directly test the importance of cytoskeletal remodeling in the hypothesized shear stress response, we briefly treated PC-3 and MDA.MB.231 cells were fully tested with cytochalasin-D prior to the shear stress protocol. During this time, cell viability was not affected by cytochalasin-D treatment. In both cell lines there was over 3-fold more cell death and an attenuated biphasic survival response in cytochalasin-D treated cells versus DMSO treated controls (FIGS. 6A-6B). Thus, shear stress-induced actin polymerization appears to play a protective role in cancer cells during conditions of flow.

Summary and Discussion

The result presented above reveal that most cancer cells, regardless of tissue origin and metastatic potential are constitutively resistant to flow conditions with wall shear forces up to ~500 dyn/cm$^2$. At increasing shear forces, up to ~6,500 dyn/cm$^2$, most of these cancer cells exhibit a biphasic loss of viability. This range of shear forces would be considered high to very high/supraphysiologic [Kamm, R. D., Cellular fluid mechanics. Annu Rev Fluid Mech, 2002. 34: p. 211-32., Schirmer, C. M. and A. M. Malek, Estimation of wall shear stress dynamic fluctuations in intracranial atherosclerotic lesions using computational fluid dynamics. Neurosurgery, 2008. 63(2): p. 326-34; discussion 334-5.]. Despite the high magnitude of these values, it is important to note that freshly prepared red and white blood cells endured these forces greater than all cell types tested. During the first two passages of shear flow (each passage roughly between 1 to 6 milliseconds), the rate of cell death is six times greater than in the subsequent eight passages. After 10 passages at the highest shear rate, the average cell death was ~60% of the total suspension. The shape of these survival curves suggests either a selective purification of inherently shear stress-resistant cells, or an adaptive resistance to shear stress. To test these possibilities, the surviving fraction of cells subjected to 10 passages of shear stress were sub-cultured and re-exposed to a second round of shear protocol. In several cancer cell lines it was shown that this approach did not enrich for shear stress-resistant cells. This finding led to the conclusion that the basis for the observed biphasic survival is an inducible and transient response rather than a stable genetic trait.

After shearing cancer cells in the presence of the membrane-impermeable dye, propidium iodide (PI), it was shown that viable cells allow rapid PI uptake during the first passage of shear stress, indicating altered membrane integrity. The rate of PI-uptake by viable cells diminishes over repeated passages, suggesting that membrane integrity was inducibly repaired and maintained after the initial "priming" round of shear stress. In support of this conclusion, cells which had been sheared several times prior to the addition of PI allowed much less of this dye in than those cells in the presence of PI throughout the assay. To gain mechanistic insight into this shear-induced resistance to continued shear stress, cells were suspended in divalent cation-free PBS. These cells were roughly 10-fold more susceptible to shear stress and had lost the biphasic survival response. When supplementing PBS suspensions with calcium or barium, it was shown that calcium addition selectively restores biphasic shear stress survival.

Whether actin polymerization in response to fluid shear stress plays a role in the inducible shear stress-resistance response was studied. Cells treated briefly with a non-cytotoxic dose of cytochalasin-D were significantly more susceptible to shear stress-induced death. Mechanical damage to plasma membranes has been shown to induce a repair response in cardiomyocytes, skeletal muscle cells, and oocytes [Terasaki, M., K. Miyake, and P. L. McNeil, Large plasma membrane disruptions are rapidly resealed by Ca2+-dependent vesicle-vesicle fusion events. J Cell Biol, 1997. 139(1): p. 63-74.]. In these cell types, extracellular calcium rapidly enters the membrane wound, triggering fusion of intercellular vesicles with the damaged plasma membrane domain. This membrane "patching" mechanism has been shown to require activation of small GTPases and rearrangements of the actinomysin cytoskeleton [Bement, W. M., et al., Rehabilitation and the single cell. Curr Opin Cell Biol, 2007. 19(1): p. 95-100.]. It is possible that cancer cells have adapted such a mechanism to overcome fluid shear stress.

Importantly, it was shown that inducible shear stress resistance is unique to transformed epithelial cells. Non-transformed cell lines and primary cells of the human breast and prostate were susceptible to magnitudes of shear force much lower than those required to induce cancer cell death. These cell types exhibited dramatically greater cell loss over the first two passages of shear flow (upwards of 90% in primary cells) and did not elaborate resistance to shear stress at later passages as seen in most carcinoma cell lines. Thus, when comparing the behavior and survival of normal epithelial cells to carcinoma cells, it can be concluded that carcinoma cells 1) have an intrinsically higher resistance to shear stress-induced cellular damage, and 2) are capable of responding to damage from shear stress, resulting in a transient but efficient repair mechanism.

Perhaps the most revealing finding of this study was that multiple cancer cell lines, derived from various tissues, and with a wide range of metastatic potential, exhibit a similar phenotype of shear stress resistance. One explanation is that the conservation of this phenotype is intimately linked to cellular transformation. Common transforming oncogenes, such as Ras, AKT, etc. result in constitutive upregulation of Rho-GTPases and changes in cytoskeletal dynamics, and thus cell morphology and tensegrity [Tzima, E., Role of small GTPases in endothelial cytoskeletal dynamics and the shear stress response. Circ Res, 2006. 98(2): p. 176-85., Cain, R. J. and A. J. Ridley, Phosphoinositide 3-kinases in cell migration. Biology of the cell/under the auspices of the European Cell Biology Organization, 2009. 101(1): p. 13-29.]. Mutations which drive primary tumor growth and invasion have been shown to co-opt for metastatic behavior, such as extravasation and angiogenesis [Gupta, G. P., et al., Mediators of vascular remodelling co-opted for sequential steps in lung metastasis. Nature, 2007. 446(7137): p. 765-70.]. The data suggest that killing of circulating tumor cells by hemodynamic shear forces is much lower than often estimated. This would argue that survival of such forces is not a large determinant of metastatic inefficiency.

The topic of metastatic inefficiency is clinically relevant to the study of circulating tumor cells (CTCs). Recently, there has been considerable interest in isolating and quantifying CTCs to develop new prognostic and predictive tools. One of the largest challenges here is that the mere presence of CTCs in the blood of patients does not always correlate with poor prognosis or metastasis. As an example, the number of circulating cells prior to surgery was shown to be predictive of relapse-free survival in breast cancer patients [Cristofanilli, M., et al., Circulating tumor cells, disease progression, and survival in metastatic breast cancer. N Engl J Med, 2004. 351(8): p. 781-91.]; and surgeries to remove non-small cell lung carcinoma have been reported to cause increased numbers CTCs in patients, which correlates with relapse [Rolle, A., et al., Increase in number of circulating disseminated epithelial cells after surgery for non-small cell lung cancer monitored by MAINTRAC® is a predictor for relapse: A preliminary report. World J Surg Oncol, 2005. 3(1): p. 18.]. Conversely, patients with ovarian or colon cancer who have surgical venous shunts, which introduce many (estimated up to millions) cancer cells into the blood every day, rarely develop metastatic disease [Tarin, D., et al., Clinicopathological observations on metastasis in man studied in patients treated with peritoneovenous shunts. Br Med J (Clin Res Ed), 1984. 288(6419): p. 749-51., Tarin, D., et al., Mechanisms of human tumor metastasis studied in patients with peritoneovenous shunts. Cancer Res, 1984. 44(8): p. 3584-92.]. These data call into question the fate of CTCs which do not complete all steps of metastasis. At the simplest level, it is likely that these cells are either eventually killed in the bloodstream or that once colonizing a secondary tissue that they are unable to proliferate sufficiently to develop into a metastases.

By extending these finding to a clinical context, it is possible that all CTCs endure shear stress quite well, regardless of their metastatic capabilities. Thus when analyzing a patient's blood for the presence of CTCs it should be considered that the absolute number of cells detected is a much less meaningful prognostic readout than understanding the ability of these circulating cells to extravasate and proliferate at a distant tissue. Furthermore, the observation that transformed cancer cell lines are considerably more resistant to shear stress than primary cells, supports the conclusion that this biology could be exploited to purify CTC preparations of non-transformed cells, improving the prognostic value of this assay.

Example 2

This example expands on the experiments described in Example 1 with additional tests of the loss in cell viability due to fluid shear stress for primary epithelial cells relative to cancerous epithelial cells.

Figure 13A:
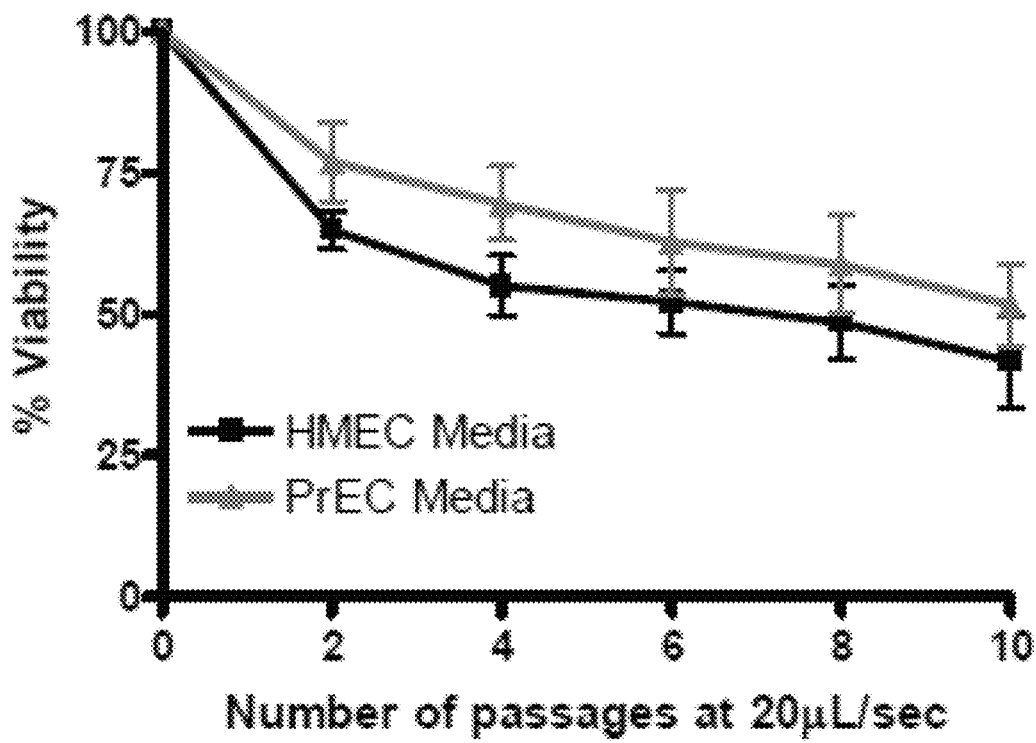
FIGS. 13A-13B show primary cell survival at 20 µL/sec. PrEC and HMEC suspensions were subjected to ten passages of FSS at 20 µL/sec.
Figure 13B:
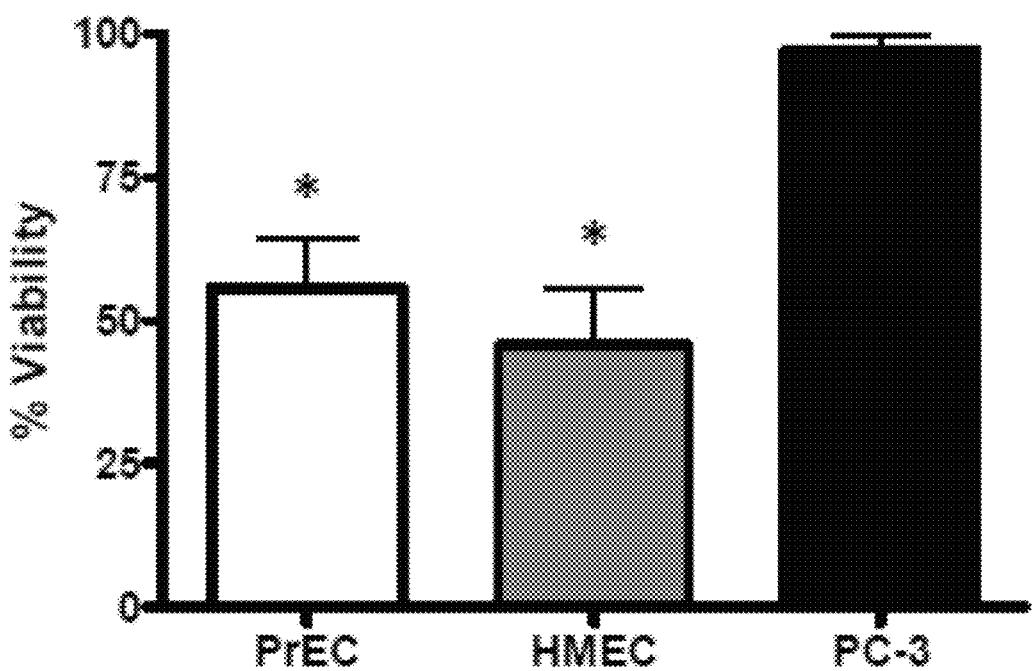

FIGS. 13A-13B shows the results of cell viability measurements for primary cells of the human breast and prostate (HMEC and PrEC, respectively) after repeated passages through the shear stress protocol at a flow rate of 20 µL/sec. Suspensions of the HMEC and PrEC cells were subjected to ten passages and viability was measured at every other passage. For the data shown, $p<0.05$ vs. PC-3 (one-way ANOVA, Bonferroni's post tests). For each cell line, n=4 experiments using the syringe pump protocol. All error bars=±SEM. As shown in FIG. 13A, at the 20 µL/sec flow rate, primary epithelial cells exhibited a pronounced, but biphasic loss of viability. In contrast, little loss in viability was observed for the PC-3 cells experiencing the same shear stress protocol, as shown in FIG. 13B.

Figure 14A:
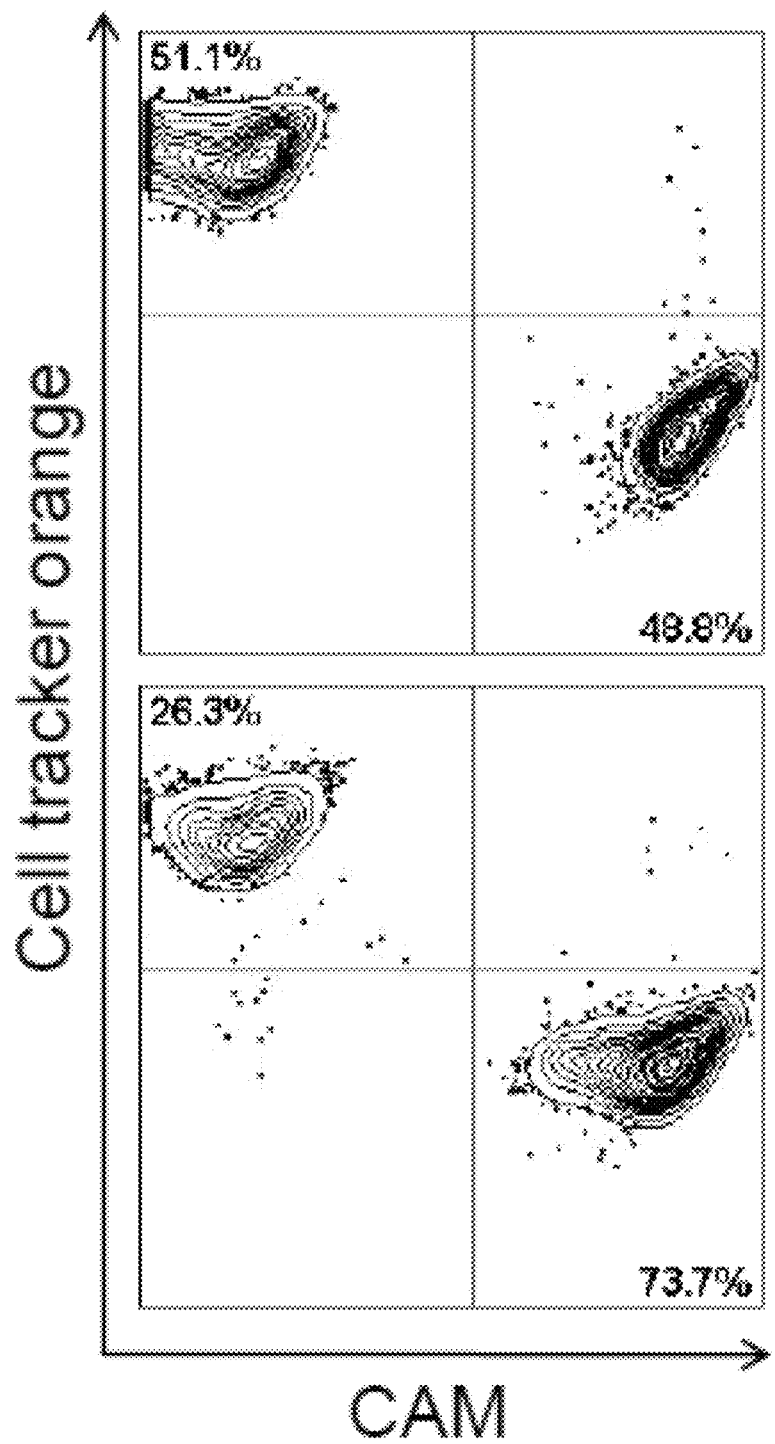
FIGS. 14A-14B show enrichment of malignant cells from a mixed cell suspension by fluid shear stress.
Figure 14B:
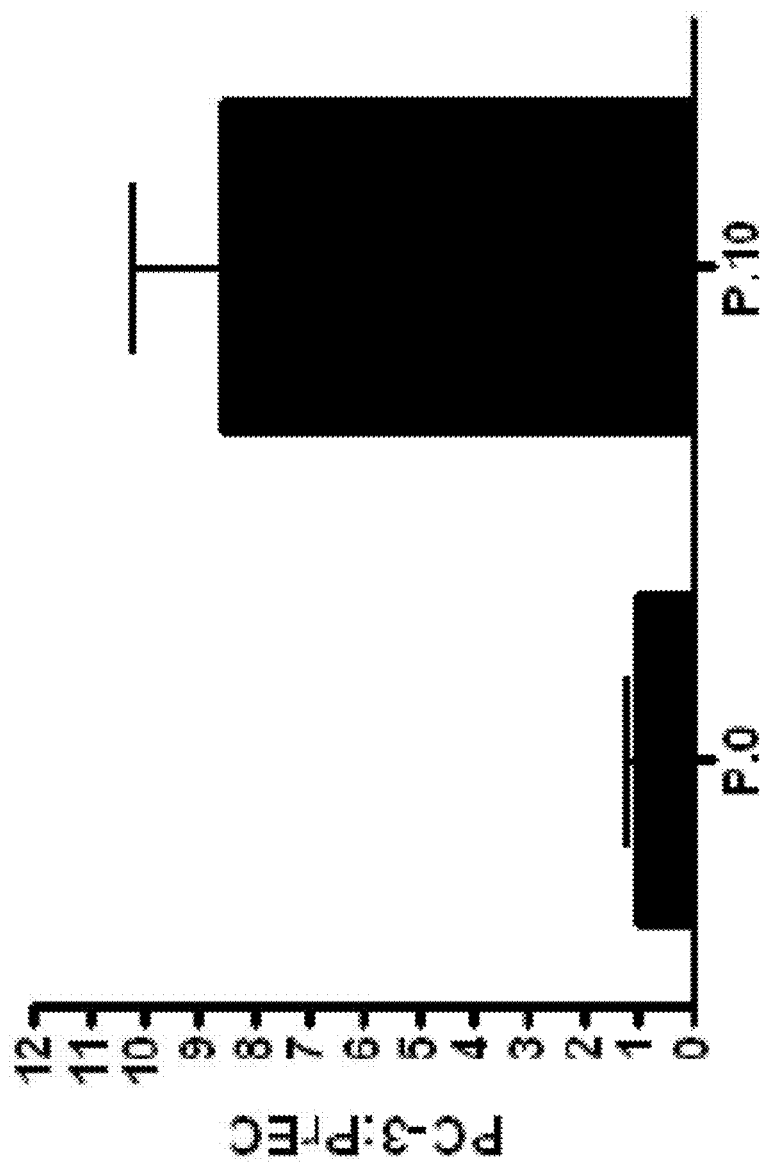

Next, the ability of the shear stress protocol to selectively kill non-cancerous cells in a fluid preparation was demonstrated by carrying out the protocol on a mixture of differentially labeled PrEC and PC-3 cells. Viability analysis of mixed cell populations: PC-3 and PrEC cells were labeled with calcein AM (Invitrogen # C34852) and cell tracker orange (Invitrogen # C2927), respectively. Suspensions, prepared as described in Example 1, were mixed ~1:1 prior to subjecting to the FSS protocol. To assess cell viability using flow cytometry, viable, calcein AM$^+$ (green) cells and viable, cell tracker orange$^+$ (orange) cells were counted. The number of green or red cells was divided by the total number (green+orange) stained viable cells counted at each passage to determine the relative numbers of each cell type in the mixture. Before (P.0) and after ten passages (P.10) of FSS, 10,000 fluorescent events were counted using flow cytometry. The results are shown in FIGS. 14A and 14B.

After exposure to FSS the ratio of PC-3 (FIG. 14A, bottom right quadrant) to PrEC (FIG. 14A, top left quadrant) changed from 0.955 to 2.80. Averaged results of three independent experiments show a change in this ratio from 1±0.07 to 3.13±SEM=0.4. See also FIG. 14B, 25 µL of mixed (PC-3:PrEC) cell suspension was plated into collagen 1-coated 8-well chamber slides before (P.0) and after ten passages (P.10) of FSS. These cells were allowed to adhere overnight and were then fixed in 4% paraformaldehyde for 10 minutes. Fixed cells were counterstained with DAPI and imaged using the Cy2 filter on a Leica DME 2500. For three separate experiments, 5 fields of view were imaged for P.0 and P.10 suspensions. At P.0 the ratio of calcein AM positive to negative cells was very close to 1. All error bars=±SEM.

Example 3

This example expands on the experiments described in Example 1 with additional tests showing that fluid shear stress resistance can be correlated to transforming oncogene, including ras, myc and PI3K. This was shown using prostate and melanoma cells specifically engineered to express transforming oncogenes.

LH, LHSR and LHMK cells were obtained from Dr. William Hahn (Dana Farber Cancer Institute) and R545 cells were obtained from Dr. Lynda Chin (Dana Farber Cancer Institute) and cultured as described in Berger R, et al. (2004) Androgen-induced differentiation and tumorigenicity of human prostate epithelial cells. *Cancer Res* 64(24):8867-8875 and Chin L, et al. (1999) Essential role for oncogenic Ras in tumour maintenance. *Nature* 400(6743):468-472. The fluid shear stress protocol and cell viability analysis were carried out as described in Example 1.

The effect of FSS (at 250 μL/sec) was compared between wild type primary human prostate epithelial cells (PrEC), immortalized PrEC (LH), and Myc/PI3K (LHMK) or Ras (LHSR) transformed PrEC. ***, p<0.001 vs. WT; #, p<0.05; ###, p<0.001 vs. LH; †, p<0.05 vs. LHSR (One way ANOVA, Bonferroni post tests). R545 melanoma cells (derived from Tyr/Tet-Ras INK4a−/−mice) express H-Rasv12 in a doxycycline-dependent manner. These cells were cultured for two passages in the presence or absence of 2 μg/mL doxycycline before shearing at 250 μL/sec. n=4 for all cell lines and conditions using syringe pump.

Figure 15A:
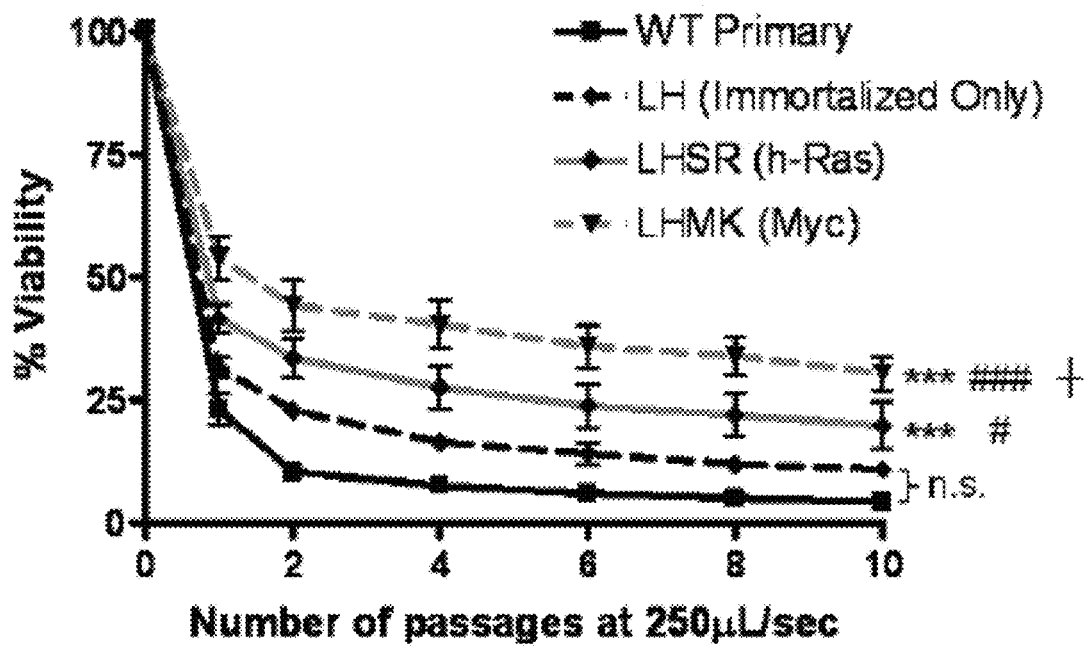
FIG. 15A shows the effect of FSS (at 250 µL/s) on wild type primary human prostate epithelial cells (PrEC), immortalized PrEC (LH), and Myc/PI3K (LHMK) or Ras (LHSR) transformed PrEC.
Figure 15B:
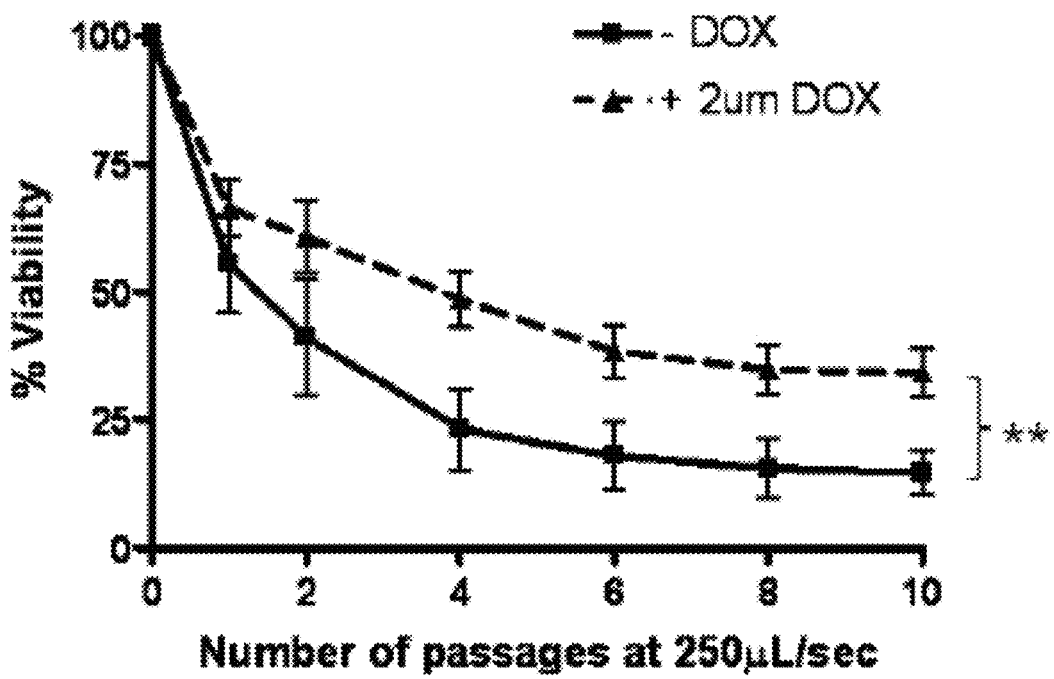
FIG. 15B shows a graph showing that R545 melanoma cells (derived from Tyr/Tet-Ras INK4a$^{-/-}$ mice) express H-Rasv12 in a doxycycline-dependent manner.

As shown in FIG. 15A, immortalization of these cells via expression of SV40 large T antigen and hTERT did not significantly affect FSS resistance, but transformation via MYC/PI3K or H-ras led to robust resistance to FSS similar to that seen in cancer cell lines. Similar result in a mouse melanoma cell line in which H-RasV12G expression is under the control of a tetracycline-inducible promoter. In the presence of doxycycline, H-Ras-expressing cells exhibited increased resistance to FSS, as shown in FIG. 15B.

The involvement of the actin cytoskeleton in FSS resistance provides an avenue to explain the role of transforming oncogenes in this process. Ras and PI3K are well known to influence cytoskeletal dynamics. Interestingly, various biophysical measurements indicate that transformed cells are more deformable (less stiff) than their non-tumorigenic counterparts. This is commonly interpreted as favoring an invasive and migratory phenotype, but such deformability may lead to susceptibility to high FSS damage, disfavoring hematogenous dissemination. Oncogenic activation may result in cells poised to rapidly mobilize the actin cytoskeleton in response to calcium influx due to high FSS.

Example 4

This example expands on the experiments described in Example 1 with additional tests showing that the loss of cell viability observed after the fluid shear stress was not a function of pH or temperature.

Figure 16A:
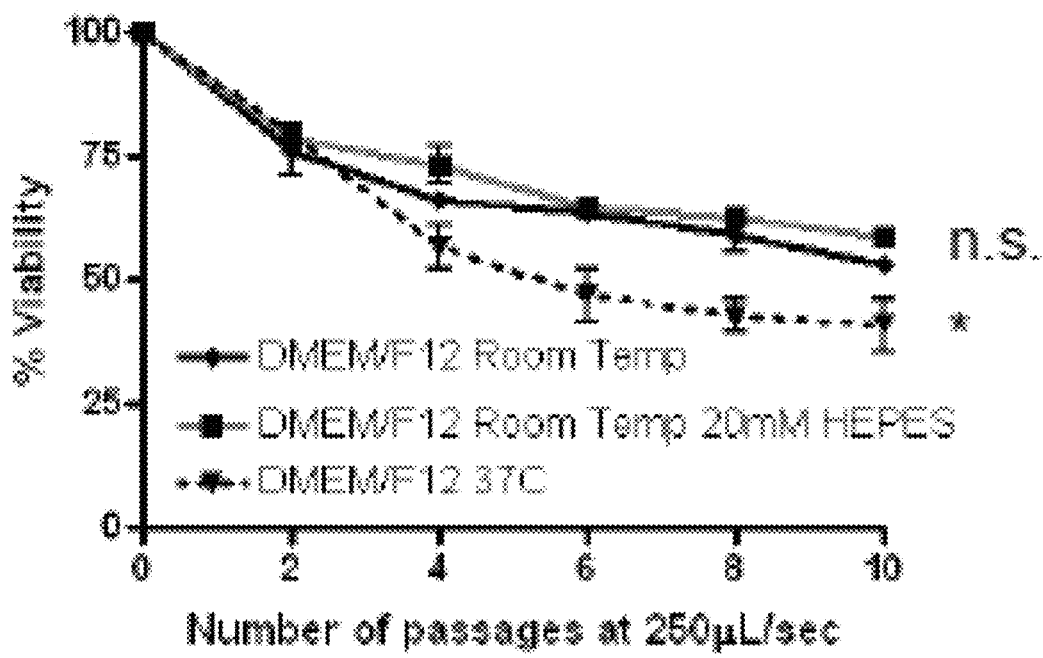
FIG. 16A shows a graph showing cell viability for PC-3 cells suspended in DMEM/F12, 10% FBS in the presence or absence of 20 mM HEPES (avg. pH at room temperature: 7.3 vs. 7.7, respectively). Also shown is the cell viability data for the PC-3 cells suspended in regular media sheared at 37° C. in a walk-in incubator.
Figure 16B:
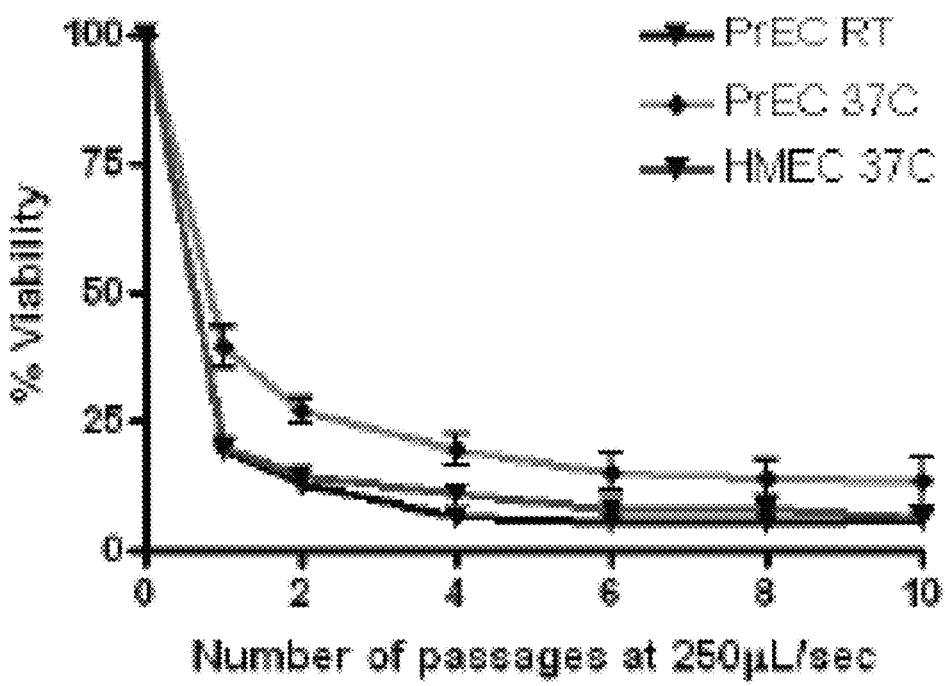
FIG. 16B shows a graph showing cell viability data for sheared primary cells (HMEC, n=2 and PrEC, n=5 experiments using pump method) at 37° C. and at room temperature.

Unlike the cancerous cells studied in the previous examples, which were in media buffered with sodium bicarbonate, PC-3 cells in this example were suspended in DMEM/F12, 10% FBS in the presence or absence of 20 mM HEPES (avg. pH at room temperature: 7.3 vs. 7.7, respectively). As shown in FIG. 16A, no significant difference in cell survival was observed under these two conditions. In addition, PC-3 cells suspended in regular media were also sheared at 37° C. in a walk-in incubator. As shown in FIG. 16A, a biphasic FSS response was still observed. *, p<0.05 vs. DMEM/F12 room temp, n=4 using the pump method (repeated measures ANOVA, Bonferroni's post tests). For comparison, primary cells (HMEC, n=2 and PrEC, n=5 experiments using pump method) were subjected to the same shear stress protocol at 37° C. and room temperature. As shown in FIG. 16B, cell survival for the primary cells was significantly reduced at both temperatures compared to their cancerous counterparts.

Example 5

This example illustrates the use of the present methods to purify a preparation comprising a fluid suspension of tumor cells isolated from a solid tumor.

Epithelial Tumor Cells Freshly Isolated from Murine Prostates Display Biphasic Loss of Viability when Exposed to Fluid Shear Stress.

Figure 17:
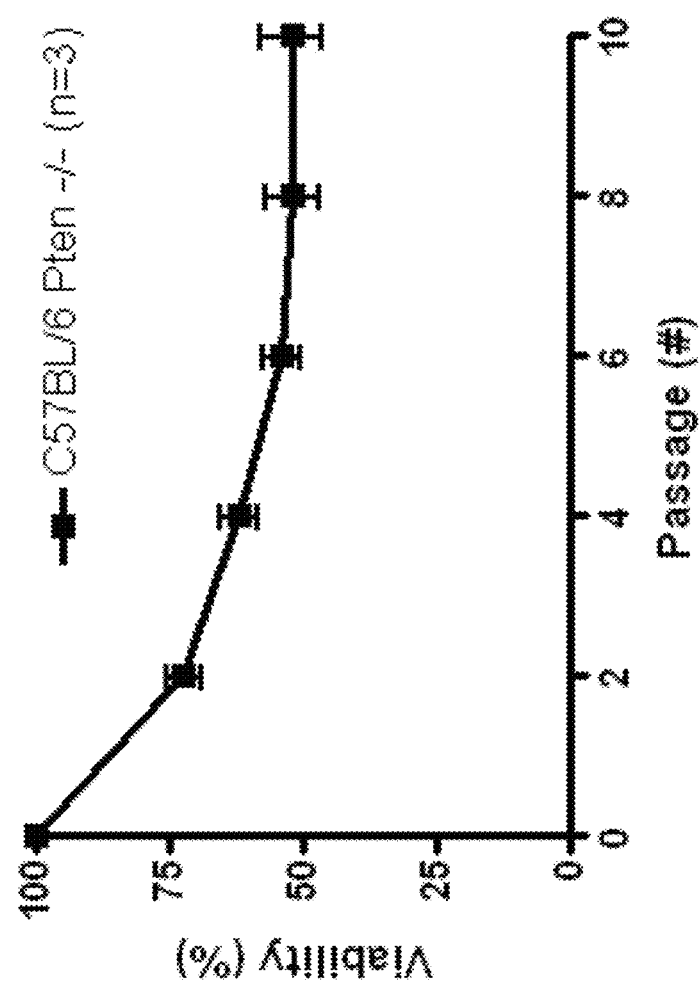
FIG. 17: Graph showing viability for cells freshly isolated from murine prostates as a function of repeated exposure to fluid shear stresses.

Aged mice harboring Pten-deficient prostates were sacrificed (details on mice as previously published in Svensson, R. U., *Am. J. Pathol.* 2011). Prostates were removed and epithelial cells isolated using a mechanical and chemical (collagenase IA) approach (see, Lukacs, R. U. et al., *Nat. Protoc.* 2010). A single cell suspension was exposed to fluid shear stress (FSS) at a flow rate of 250 μl/sec according to the methods presented in Example 1. Viability was assessed by bioluminescence imaging by virtue of a prostate epithelium-specific expression of luciferase. As previously demonstrated in transformed cultured cells, these transformed cells exhibit the biphasic survival curve indicative of an early FSS-induced elaboration of resistance to subsequent exposures to FSS. This data, which is shown in FIG. 17, supports the conclusion that inducible resistance is conferred by transformation, rather than an artifact of in vitro culture. Furthermore, it demonstrates that the present methods can be used for quickly distinguishing benign from malignant cells from clinical biopsies.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for purifying a fluid sample comprising contacting viable cancerous cells, viable normal cells and extracellular calcium with a micro fluidic device comprising:
    (a) a conduit configured to contain the fluid sample; and
    (b) a motorized pump operably coupled to the conduit, the motorized pump configured to pass the fluid sample through the conduit at a flow rate,
        wherein the conduit and the motorized pump are configured to apply an initial pulse of fluid shear stress to the fluid sample in vitro, said initial pulse of fluid shear stress sufficient to induce a fluid shear stress resistance in the viable cancerous cells such that the magnitude of shear stress required to kill the viable cancerous cells is greater than the magnitude of shear stress required to kill the viable normal cells; and
        wherein the conduit and the motorized pump are configured to subsequently apply one or more additional pulses of fluid shear stress to the fluid sample in vitro, said fluid shear stress sufficient to selectively kill the viable normal cells relative to the viable cancerous cells such that a ratio of the viable cancerous cells to the viable normal cells is increased;

applying an initial pulse of fluid shear stress to the fluid sample, wherein the initial pulse of fluid shear stress induces a fluid shear stress resistance in the viable cancerous cells such that the magnitude of shear stress required to kill the viable cancerous cells is greater than the magnitude of shear stress required to kill the viable normal cells; and subsequently applying one or more additional pulses of fluid shear stress to the fluid sample comprising the fluid shear stress-resistant viable cancerous cells, said fluid shear stress sufficient to selectively kill the viable normal cells relative to the viable cancerous cells, whereby the ratio of viable cancerous cells to viable normal cells in the preparation is increased.

2. The method of claim 1, wherein the ratio of the viable cancerous cells to the viable normal cells in the fluid sample is at least doubled.

3. The method of claim 1, wherein a percent viability for the viable cancerous cells is at least 40% and the percent viability for the viable normal cells is no greater than 20% substantially immediately following the application of the initial and additional pulses of fluid shear stress, wherein percent viability is determined as the percent viability relative to a control maintained without the application of shear stresses for the duration of the pulse applications.

4. The method of claim 1, wherein the initial and additional pulses of fluid shear stress apply a fluid shear stress in the range from about 300 dyn/cm$^2$ to about 6500 dyn/cm$^2$.

5. The method of claim 1, wherein the initial and additional pulses of fluid shear stress apply a fluid shear stress in the range from about 500 dyn/cm$^2$ to about 6500 dyn/cm$^2$.

6. The method of claim 1, wherein the additional pulses apply a supra-physiologic level of fluid shear stress.

7. The method of claim 1, wherein the motorized pump is configured to pass the fluid sample through the conduit at a substantially constant flow rate.

8. The method of claim 1, wherein the initial pulse and the one or more additional pulses each have a duration of no greater than about 20 msec.

9. The method of claim 1, wherein the initial pulse and the one or more additional pulses each have a duration in the range of from about 0.5 msec to about 20 msec.

* * * * *